(12) United States Patent
Dockendorff et al.

(10) Patent No.: US 7,946,169 B2
(45) Date of Patent: *May 24, 2011

(54) FLUID LEVEL DETECTOR

(75) Inventors: James B. Dockendorff, North Haven, CT (US); Kevin B. Downs, Coventry, CT (US); Bryan M. LaBarge, Terryville, CT (US); George K. Lewis, Andover, MA (US)

(73) Assignee: Gems Sensors, Inc., Plainville, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/563,380

(22) Filed: Sep. 21, 2009

(65) Prior Publication Data
US 2010/0005878 A1    Jan. 14, 2010

Related U.S. Application Data

(63) Continuation of application No. 11/595,494, filed on Nov. 10, 2006, now Pat. No. 7,607,347.

(60) Provisional application No. 60/779,951, filed on Mar. 7, 2006.

(51) Int. Cl.
*G01F 23/28* (2006.01)

(52) U.S. Cl. ..................... 73/290 V

(58) Field of Classification Search ........... 73/290 V
See application file for complete search history.

(56) References Cited

U.S. PATENT DOCUMENTS

| | | |
|---|---|---|
| 2,990,543 A | 6/1961 | Rod |
| 3,693,445 A | 9/1972 | Johnson |
| 4,144,517 A | 3/1979 | Baumoel |
| 4,183,249 A | 1/1980 | Anderson |
| 4,280,126 A | 7/1981 | White |
| 4,531,406 A | 7/1985 | Fritz |
| 4,580,448 A | 4/1986 | Skrgatic |
| 4,630,245 A | 12/1986 | Dam |
| 4,815,323 A | 3/1989 | Ellinger et al. |
| 4,823,801 A | 4/1989 | Sakane |
| 4,901,245 A | 2/1990 | Olson et al. |
| 4,911,170 A | 3/1990 | Thomas et al. |
| 4,934,191 A | 6/1990 | Kroening et al. |
| 4,961,456 A | 10/1990 | Stembridge et al. |
| 5,031,451 A | 7/1991 | Webster |
| 5,094,108 A | 3/1992 | Kim et al. |
| 5,105,661 A | 4/1992 | Sekita et al. |

(Continued)

FOREIGN PATENT DOCUMENTS

EP    0676624    10/1995

(Continued)

*Primary Examiner* — John Fitzgerald
(74) *Attorney, Agent, or Firm* — Nelson Mullins Riley & Scarborough, LLP

(57) ABSTRACT

A fluid detector includes a piezoelectric element that outputs a first ultrasonic signal in response to an input electrical signal and a lens with an upper portion and a lower portion. A housing is integral with an outer surface of the wall of a container and defines a cylindrical central bore for receiving the lens. The piezoelectric element is coupled to the upper portion of the lens so that the lens focuses the first ultrasonic signal toward the wall so that it enters the wall. An ultrasonic detector is disposed adjacent the outer surface of the wall, for receiving a second ultrasonic signal from the wall that results from the first ultrasonic signal and that is affected by the presence or absence of fluid. The ultrasonic detector generates an output electrical signal corresponding to the second ultrasonic signal.

20 Claims, 16 Drawing Sheets

U.S. PATENT DOCUMENTS

| | | | |
|---|---|---|---|
| 5,195,058 A | 3/1993 | Simon | |
| 5,264,831 A | 11/1993 | Pfeiffer | |
| 5,438,868 A | 8/1995 | Holden et al. | |
| 5,586,085 A | 12/1996 | Lichte | |
| 5,663,503 A | 9/1997 | Dam et al. | |
| 5,697,248 A | 12/1997 | Brown | |
| 5,730,025 A | 3/1998 | Getman et al. | |
| 5,755,136 A | 5/1998 | Getman et al. | |
| 5,836,192 A | 11/1998 | Getman et al. | |
| 5,922,961 A | 7/1999 | Hsu et al. | |
| 6,053,041 A | 4/2000 | Sinha | |
| 6,412,344 B1 | 7/2002 | Danicich et al. | |
| 6,435,024 B1 | 8/2002 | Alvarez et al. | |
| 6,529,845 B1 | 3/2003 | Beck | |
| 6,536,275 B1 | 3/2003 | Durkee et al. | |
| 6,631,639 B1 | 10/2003 | Dam et al. | |
| 6,938,995 B2 | 9/2005 | Mutz et al. | |
| 7,328,611 B2 | 2/2008 | Klees et al. | |
| 7,360,417 B2 | 4/2008 | Dockendorff et al. | |
| 2008/0051680 A1 | 2/2008 | Luebcke | |

FOREIGN PATENT DOCUMENTS

| | | |
|---|---|---|
| GB | 2050604 | 1/1981 |
| GB | 2302946 | 2/1997 |
| WO | 93/02340 | 2/1993 |

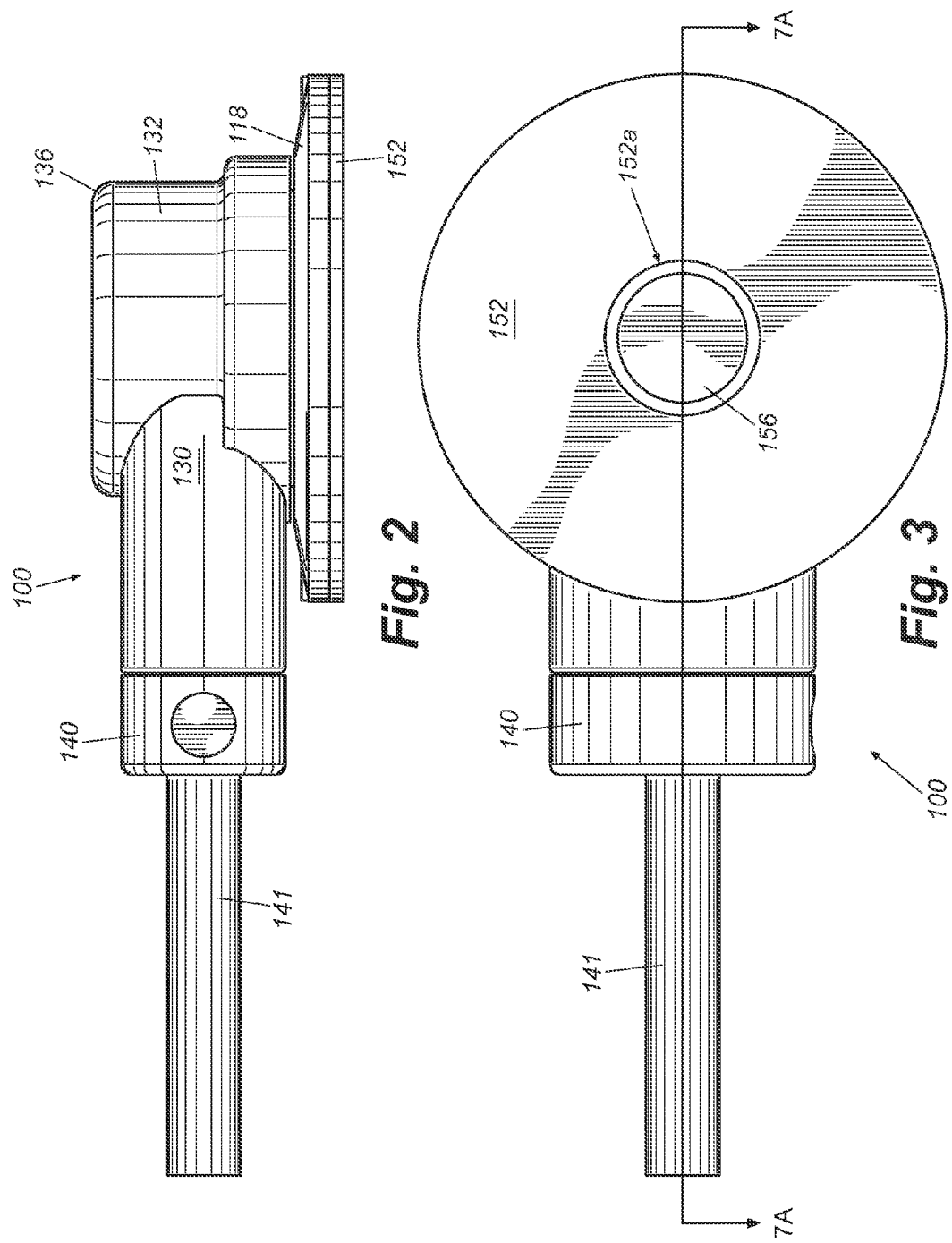

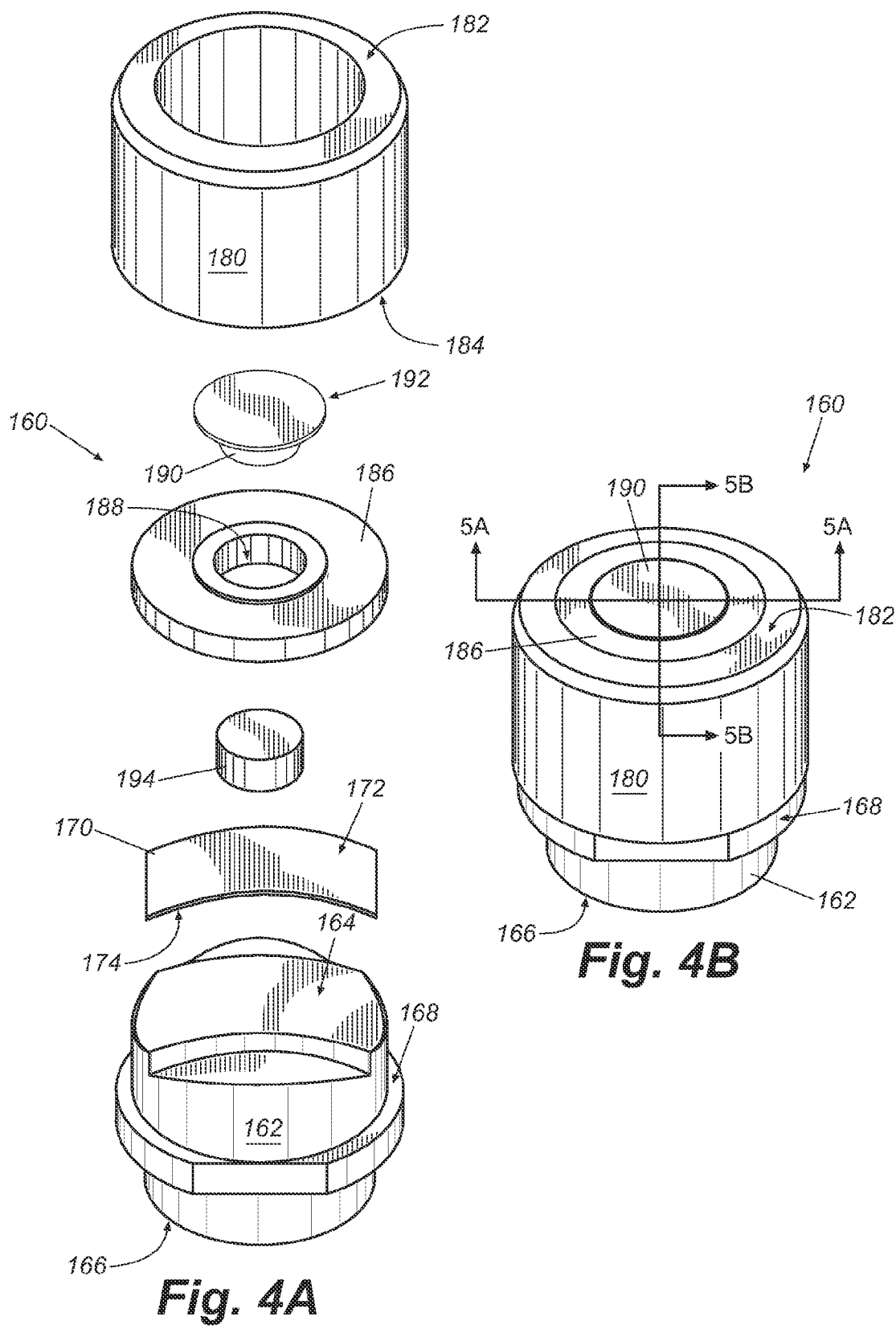

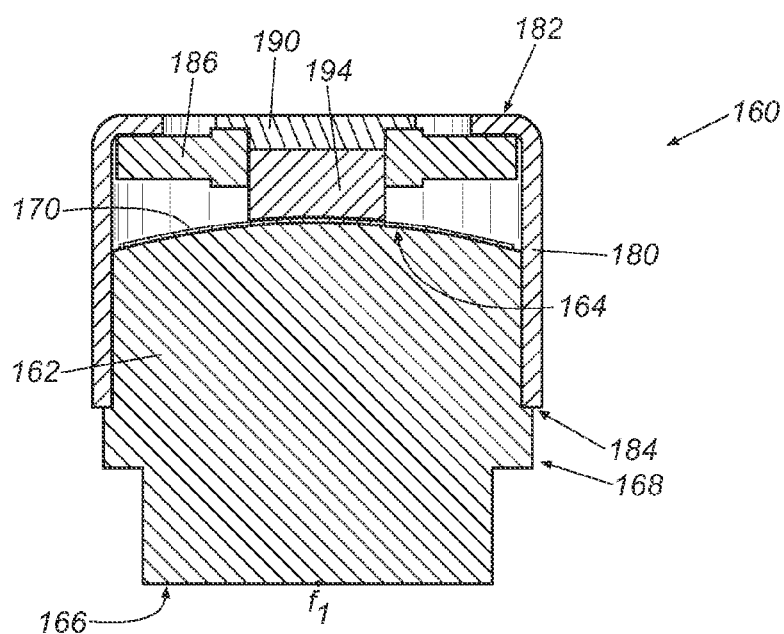
Fig. 5A
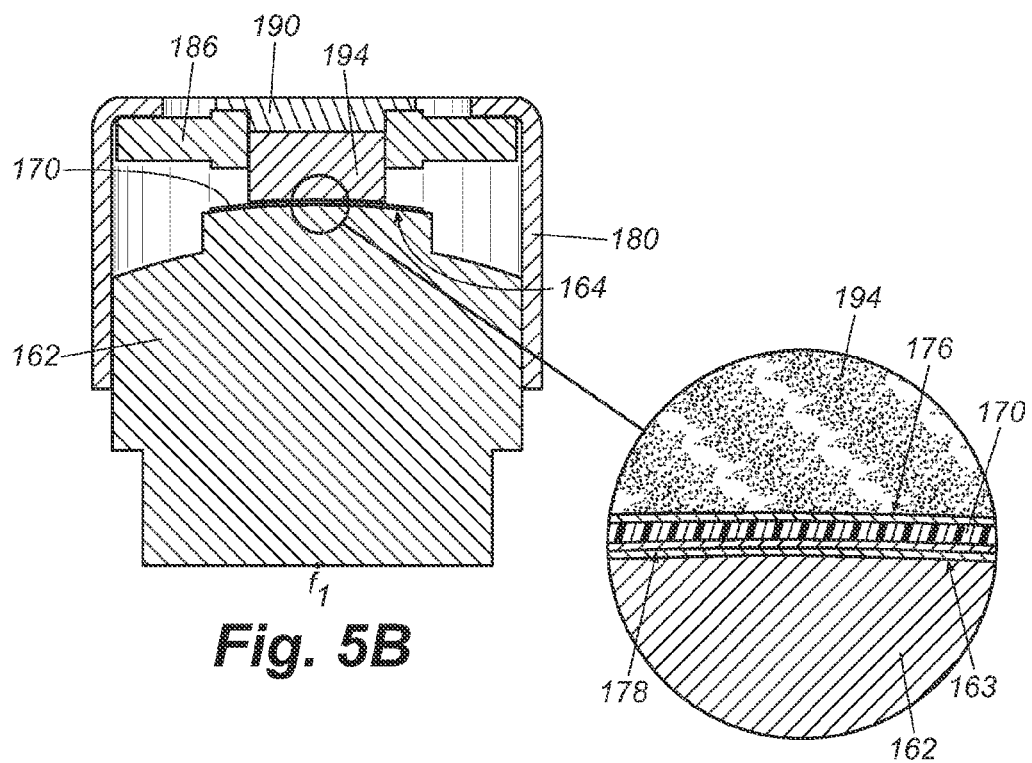
Fig. 5B
Fig. 6

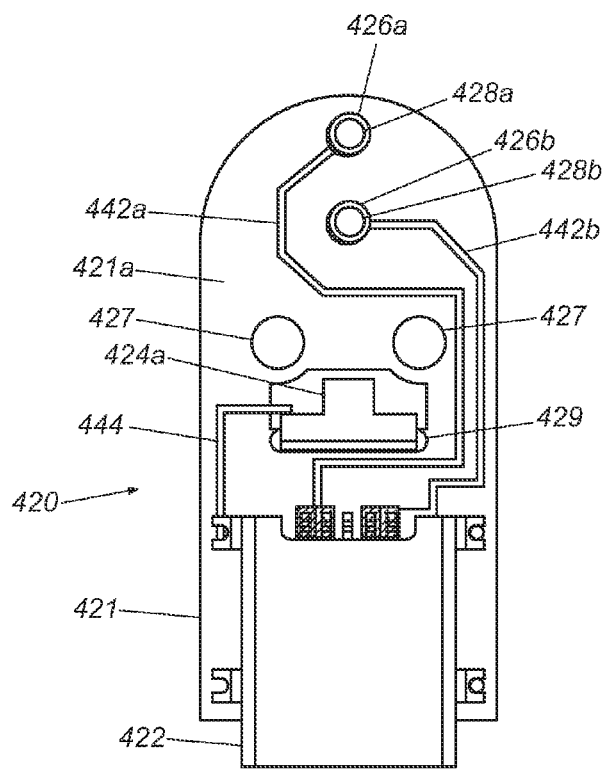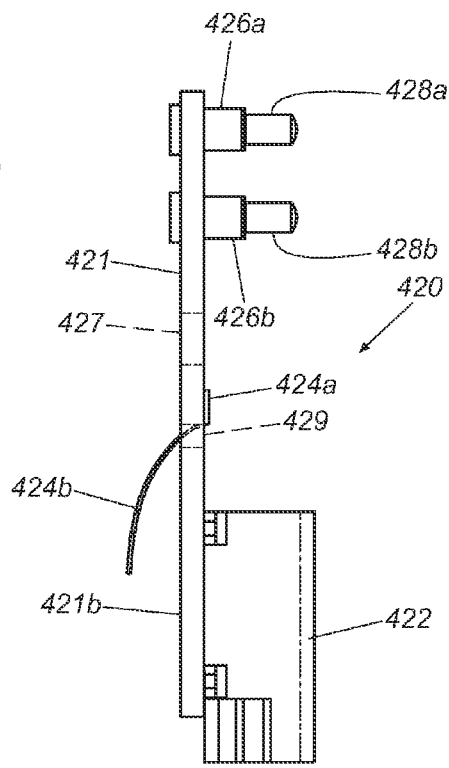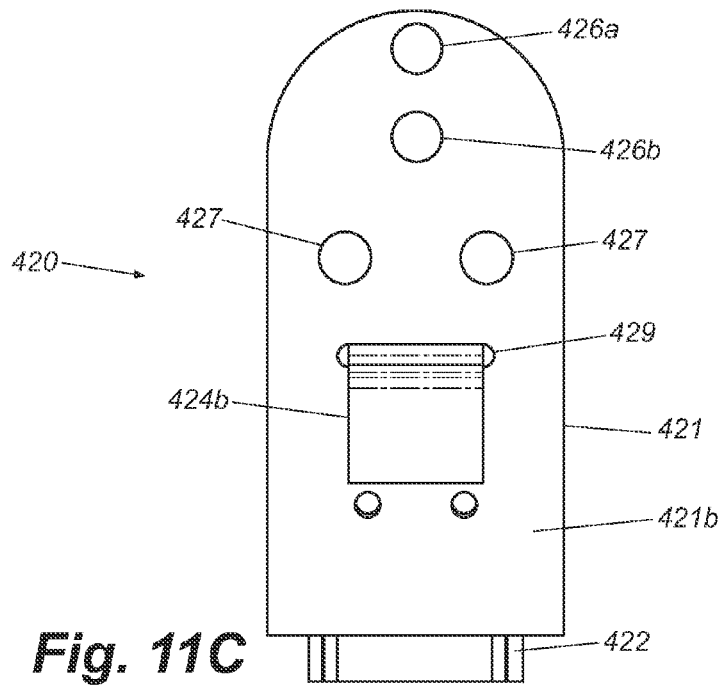

FLUID LEVEL DETECTOR

CLAIM OF PRIORITY

This application is a continuation of U.S. patent application Ser. No. 11/595,494, filed Nov. 10, 2006, now U.S. Pat. No. 7,607,347, which claims priority to U.S. Provisional Patent Application Ser. No. 60/779,951, filed Mar. 7, 2006, the entire disclosures of which are incorporated by reference herein.

FIELD OF THE INVENTION

The present disclosure relates generally to fluid level detectors for use with various sized containers. More particularly, the present disclosure relates to a fluid level detector including a piezoelectric element that may be used to determine the presence or absence of a fluid within the container to which the fluid level detector is attached.

BACKGROUND OF THE INVENTION

The use of piezoelectric materials in fluid level sensors is known. An existing design includes two piezoelectric sensor elements mounted opposite each other on the inside of a container. The sensor elements are both mounted at the level of interest. A first sensor element functions as a transmitter and is electrically excited with a voltage pulse or continuous frequency such that it transmits an acoustic signal. The second sensor element functions as a receiver of the transmitted acoustic signal. When both sensor elements are immersed in a fluid, the acoustic signal generated by the first sensor propagates through the fluid and is detected by the second sensor element, thereby indicating the presence of fluid at the level of the sensor elements. In the presence of air, the acoustic signal is not detected by the second sensor element, indicating that fluid is not present at the level of interest.

As noted, existing fluid level sensors often require intimate contact between the sensor elements and the fluid being detected. As well, because the sensor elements are typically mounted inside the container, the structural integrity of the container must be breached to install the sensor elements. As such, the container must usually be empty, or at least not have fluids at or above the level of interest, when the sensor elements are being installed.

SUMMARY OF THE INVENTION

The present disclosure recognizes and addresses the foregoing considerations, and others, of prior art constructions and methods. Accordingly, it is an object of the present disclosure to provide an improved fluid level detector.

The present disclosure includes a fluid detector for determining a presence of a fluid within a container, the container having a wall with an outer surface and an inner surface. The fluid detector includes a piezoelectric element that outputs a first ultrasonic signal in response to an input electrical signal and a lens with an upper portion and a lower portion. A generally cylindrical wall is integral with and extends outwardly from the outer surface of the wall of the container. The generally cylindrical wall defines a housing with a cylindrical central bore with a base surface adjacent the outer surface of the wall of the container. The piezoelectric element is coupled to the upper portion of the lens so that, when the lens is disposed within the cylindrical central bore adjacent the base surface such that the lens is intermediate the piezoelectric element and the wall, the lens focuses the first ultrasonic signal toward the wall so that the first ultrasonic signal enters the wall. The fluid detector further includes an ultrasonic detector that, when disposed in a predetermined position adjacent the outer surface of the wall, receives a second ultrasonic signal from the wall that results from the first ultrasonic signal and that is affected in a predetermined manner by presence or absence of fluid at the inner surface of the wall. The ultrasonic detector generates an output electrical signal corresponding to the second ultrasonic signal.

Another embodiment of the present disclosure includes a fluid detector for determining a presence of a fluid within a container. The fluid detector includes a container with a wall with an outer surface and an inner surface. A portion of the wall extends outwardly from the outer surface of the wall and defines a housing with a cylindrical central bore with a base surface disposed proximal to the wall of the container. The fluid detector also includes a piezoelectric element that outputs a first ultrasonic signal in response to an input electrical signal and a lens with an upper portion and a lower portion. The piezoelectric element is coupled to the upper portion of the lens so that, when the lens is disposed within the cylindrical central bore such that the lens is intermediate the piezoelectric element and the wall, the lens focuses the first ultrasonic signal toward the wall so that the first ultrasonic signal enters the wall. The fluid detector further includes an ultrasonic detector that, when disposed in a predetermined position adjacent the outer surface of the wall, receives a second ultrasonic signal from the wall that results from the first ultrasonic signal and that is affected in a predetermined manner by presence or absence of fluid at the inner surface of the wall. The ultrasonic detector generates an output electrical signal corresponding to the second ultrasonic signal.

The accompanying drawings, which are incorporated in and constitute a part of this specification, illustrate embodiments of the fluid level detector and, together with the description, serve to explain the principles of the fluid level detector.

BRIEF DESCRIPTION OF THE DRAWINGS

A full and enabling disclosure of the fluid level detector, including the best mode thereof to one of ordinary skill in the art, is set forth more particularly in the remainder of the specification, which makes reference to the accompanying figures, in which;

FIG. 2 is a side view of the assembled fluid level detector as shown in FIG. 1;

FIG. 3 is a bottom view of the assembled fluid level detector as shown in FIG. 1;

FIG. 4A is an exploded, perspective view of a sensor assembly of the level detector as shown in FIG. 1;

FIG. 4B is a top perspective view of the assembled sensor assembly as shown in FIG. 4A;

FIG. 5A is a side, cross-sectional view of the sensor assembly as shown in FIG. 4B, taken along line 5A-5A;

FIG. 5B is a side, cross-sectional view of the sensor assembly as shown in FIG. 4B, taken along line 5B-5B;

FIG. 6 is a detailed, partial cross-sectional view of the sensor assembly as shown in FIG. 5B;

FIGS. 11A through 11C are front, side and back views of a printed circuit board with electrical connectors as shown in FIG. 8;

Figure 1:
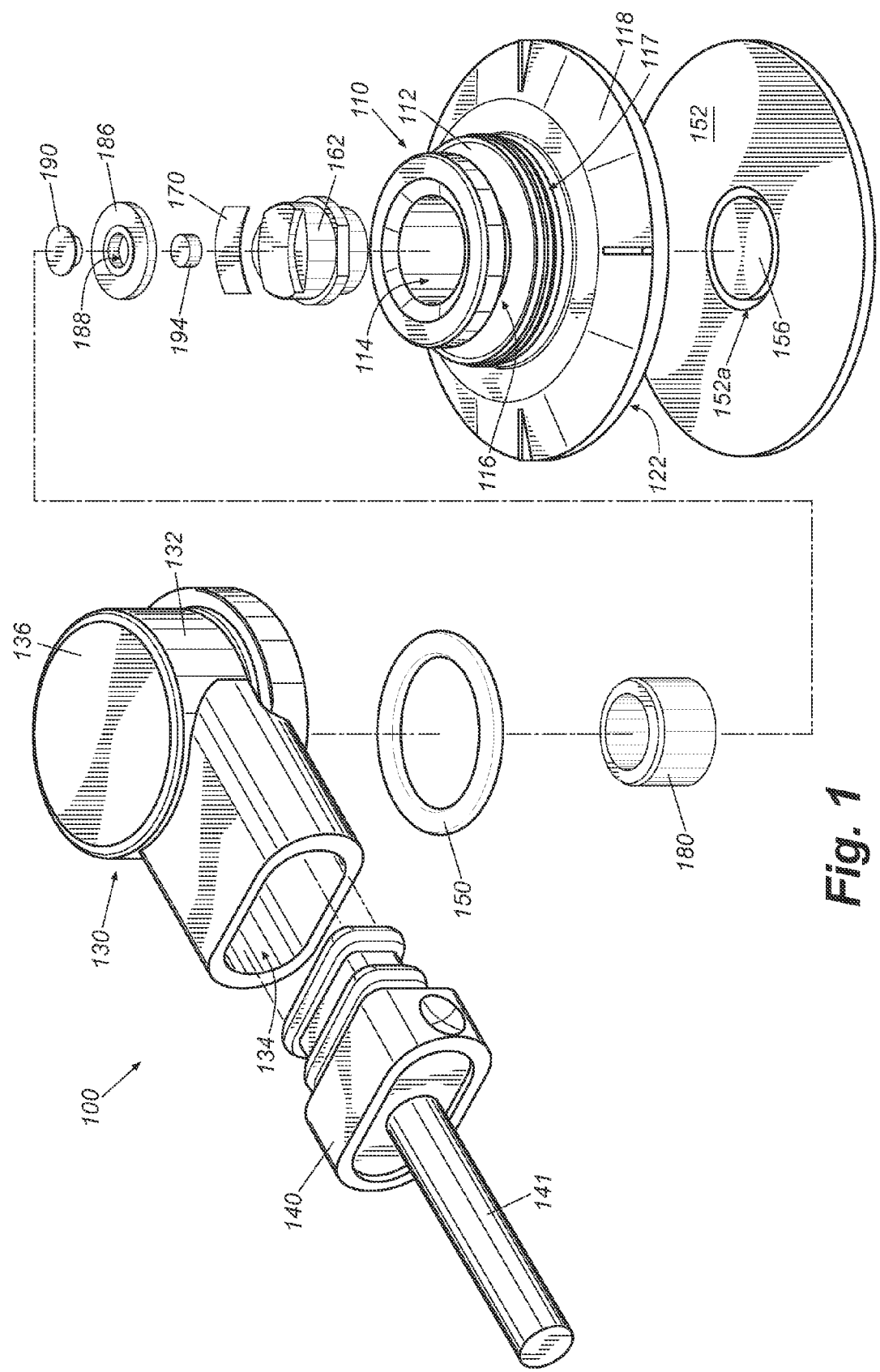
FIG. 1 is an exploded, perspective view of a fluid level detector in accordance with an embodiment of the present disclosure.

Repeat use of reference characters in the present specification and drawings is intended to represent same or analogous features or elements of the fluid level detector according to the disclosure.

DETAILED DESCRIPTION OF THE PREFERRED EMBODIMENTS

Reference will now be made in detail to presently preferred embodiments of the fluid level detector, one or more examples of which are illustrated in the accompanying drawings. Each example is provided by way of explanation, not limitation, of the fluid level detector. In fact, it will be apparent to those skilled in the art that modifications and variations can be made in the present fluid level detector without departing from the scope or spirit thereof. For instance, features illustrated or described as part of one embodiment may be used on another embodiment to yield a still further embodiment. Thus, it is intended that the present disclosure covers such modifications and variations as come within the scope of the appended claims and their equivalence.

Referring now to FIG. 1, a fluid level detector 100 includes a bottom housing 110, a top housing 130, a wiring harness 140, and a sensor assembly 160 (FIGS. 4A and 4B). As described in more detail below, sensor assembly 160 comprises an ultrasonic transducer. Bottom housing 110 includes a generally cylindrical upper wall 112 and a disc-shaped base 118. Upper wall 112 defines a generally cylindrical central bore 114 disposed about the longitudinal center axis of bottom housing 110. Upper wall 112 further includes an annular groove 116 extending inwardly from its outer surface and an annular lip 117 extending outwardly from its outer surface. Base 118 defines an aperture 120 (FIG. 7A) that it is in communication with the central bore 114 and a bottom surface 122 that is configured for abutment with a container wall 104 (FIG. 7B). Aperture 120 is transverse to the longitudinal center axis of central bore 114 and has a diameter that is smaller than the diameter of central bore 114.

Top housing 130 includes a top portion 136 and a substantially cylindrical wall 132 extending downwardly therefrom. Cylindrical wall 132 is configured to slidably receive upper wall 112 of bottom housing 110. An annular groove 133 (FIGS. 7A and 7B) extends outwardly into the cylindrical wall 132 of top housing 130 and is located and configured such that when upper wall 112 of bottom housing 110 is adequately inserted into cylindrical wall 132, annular lip 117 on upper wall 112 is firmly seated in annular groove 133, thereby securing bottom housing 110 and top housing 130 together. A wiring harness receptacle 134 for slidably receiving wiring harness 140 is formed in cylindrical wall 132. Preferably, both bottom housing 110 and top housing 130 are formed from molded polymers such as, but not limited to acrylonitrile butadiene styrene. However, it should be appreciated that any suitable material could be utilized.

Prior to assembling bottom housing 110 and top housing 130, an O-ring 150 is positioned in annular groove 116 of upper wall 112. O-ring 150 serves to prevent dirt, debris, and humidity from entering fluid level detector 100 after bottom and top housings 110 and 130 are assembled.

Referring now to FIGS. 4A and 4B, transducer 160 includes a lens 162, a piezoelectric element 170, a conductive sleeve 180, an insulative disc 186, a tab contact 190, and a conductive pad 194. Lens 162 is generally cylindrical in shape and includes an annular ledge 168 disposed between upper and lower portions of lens 162 and extending radially from the main body of the lens. The upper portion of lens 162 includes a domed surface 164 having a conductive layer 163 (FIG. 6) formed thereon. The lower portion of lens 162 defines a contact face 166 that abuts a container wall 104 (FIG. 7B) when fluid level detector 100 is installed for operation. Preferably, lens 162 is formed of a material exhibiting low acoustic loss and an acoustic impedance similar to that of piezoelectric element 170 and container wall 104. Preferably, lens 162 is constructed of polystyrene, REXOLITE, or other similar materials. As well, an example of a suitable material for conductive layer 163 is copper, although it should be appreciated that many materials exhibit suitable electrical conductivity and could be utilized.

Piezoelectric element 170 is preferably a flexible piezoelectric film element (preferably a suitably processed polyvinylidene fluoride copolymer (PVDF)) having a top surface 172 and a bottom surface 174. A first electrode layer 176 (FIG. 6) and a second electrode layer 178 (FIG. 6) are formed on top and bottom surfaces 172 and 174, respectively. First and second electrode layers 176 and 178 are isolated electrically from each other by piezoelectric film element 170. Because piezoelectric film element 170 is flexible, it conforms to the shape of domed surface 164 of lens 162 when secured thereto.

Conductive sleeve 180 is substantially cylindrical and includes an inwardly depending lip 182 at the top end and an edge 184 at the bottom end that is configured to abut annular ledge 168 of lens 162 when transducer 160 is assembled. Further, the inner diameter of conductive sleeve 180 is slightly larger than the outer diameter of the upper portion of lens 162 such that lens 162 is partially insertable into conductive sleeve 180. Preferably, conductive sleeve 180 is formed of stainless steel, or other similarly conductive materials.

Insulative disc 186 defines a central aperture 188 that is configured to receive a portion of tab contact 190. The outer diameter of insulated disc 186 is slightly less than the inner diameter of conductive sleeve 180 such that insulative disc 186 can be disposed inside conductive sleeve 180, adjacent inwardly depending lip 182. Disc 186 is formed of any material suitable for the purpose of insulating conductive sleeve 180 from tab contact 190, preferably a polymer such as, but not limited to, acrylonitrile butadiene styrene, for example marketed under the name CYOLAC MG94 by GE Plastics.

Tab contact 190 includes a portion that is insertable into central aperture 188 of disc 186 and a planar surface 192 having a diameter greater than that of central aperture 188. As such, planar surface 192 prevents the passage of tab contact 190 through central aperture 188. Preferably, tab contact 190 is formed of nickel plated brass. However, other similarly electrically conductive materials are acceptable. A conductive pad 194 is comprised of foam with a nickel plating and has an outer diameter such that it is at least partially insertable into central aperture 188 of insulative disc 186. Although plated, conductive pad 194 remains pliant and thereby facilitates electrical contact of conductive pad 194 with both piezoelectric film element 170 and tab contact 190. After transducer 160 is assembled, piezoelectric film element 170 is disposed between domed surface 164 of lens 162 and conductive pad 194 (FIG. 6).

As previously noted, and referring also to FIG. 6, piezoelectric film element 170 includes first and second electrode layers 176 and 178 formed respectively on top and bottom surfaces 172 and 174 of piezoelectric film element 170. During assembly, piezoelectric film element 170 is adhesively secured to domed surface 164 such that second electrode layer 178 and conductive layer 163 are adjacent to and in electrical contact with each other, as best shown in FIG. 6. Preferably, piezoelectric film element 170 is secured to domed surface 164 with cynoacrylate, although other adhesives, such as silver filled epoxies are acceptable. When securing piezoelectric film element 170 to domed surface 164, electrical contact is maintained between second electrode layer 178 and conductive layer 163 by mechanical contact.

First and second electrode layers 176 and 178 are formed by plating opposing sides of piezoelectric film element 170 with a combination of platinum and gold, and conductive layer 163 is formed on domed surface 164 from copper. These materials are merely provided as examples of suitable coatings, although it should be noted that other similarly conductive materials can be used in other embodiments. Preferred piezoelectric film element 170 is a PVDF film as available from Ktech, Inc., 1300 Eubank Blvd., SE, Albuquerque, N.M., 87123-3336. Although embodiments are envisioned wherein multiple transducers 160 are used in combination to detect the presence of fluids, preferred embodiments utilize a single transducer 160 wherein lens 162 and piezoelectric film element 170 not only transmit acoustic signals, but also act as an ultrasonic receiver for detecting return signals.

Next, insulative disc 186 is secured inside conductive sleeve 180 adjacent inwardly depending lip 182. As noted, conductive sleeve 180 is comprised of stainless steel, and insulative disc 186 is formed of a polymer. Insulative disc 186 is secured to conductive sleeve 180 adjacent inwardly depending lip 182 by dimpling conductive sleeve 180 such that it grips insulative disk 186. However, various methods, such as gluing or tacking, are acceptable for use with various other embodiments. Tab contact 190 is inserted into central aperture 188 of insulative disc 186, and conductive pad 194 is secured to the bottom portion of contact tab 190 by a conductive, pressure-sensitive adhesive (not shown). As such, conductive pad 194 extends downwardly from tab contact 190 and into the interior of conductive sleeve 180.

Conductive sleeve 180 is passed over the upper portion of lens 162 until bottom edge 184 of conductive sleeve 180 abuts lens annular ledge 168. Once positioned, conductive sleeve 180 is dimpled about lower edge 184 so that it grips lens 162. So positioned, conductive pad 194 is in mechanical and electrical contact with first electrode layer 176 of piezoelectric film element 170, as best seen in FIG. 6.

Figure 7A:
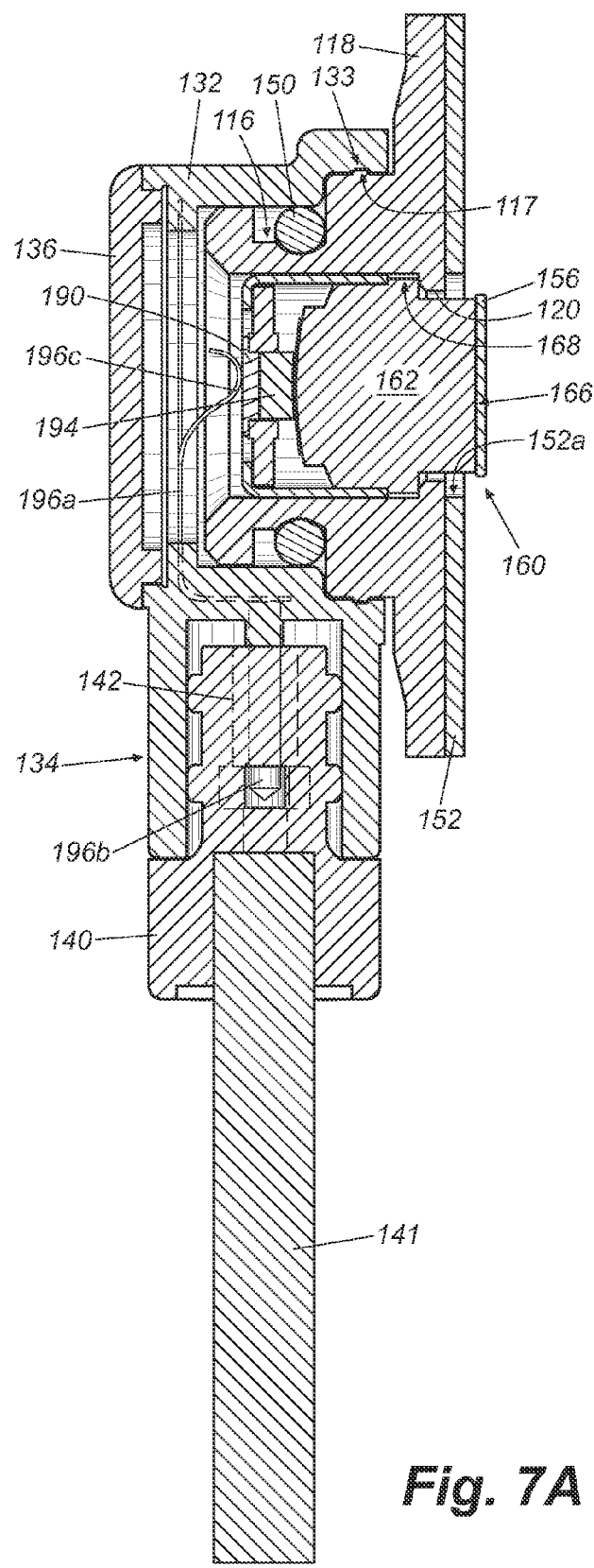
FIG. 7A is a side, cross-sectional view of the fluid level detector as shown in FIG. 3, along line 7A-7A.
Figure 7B:
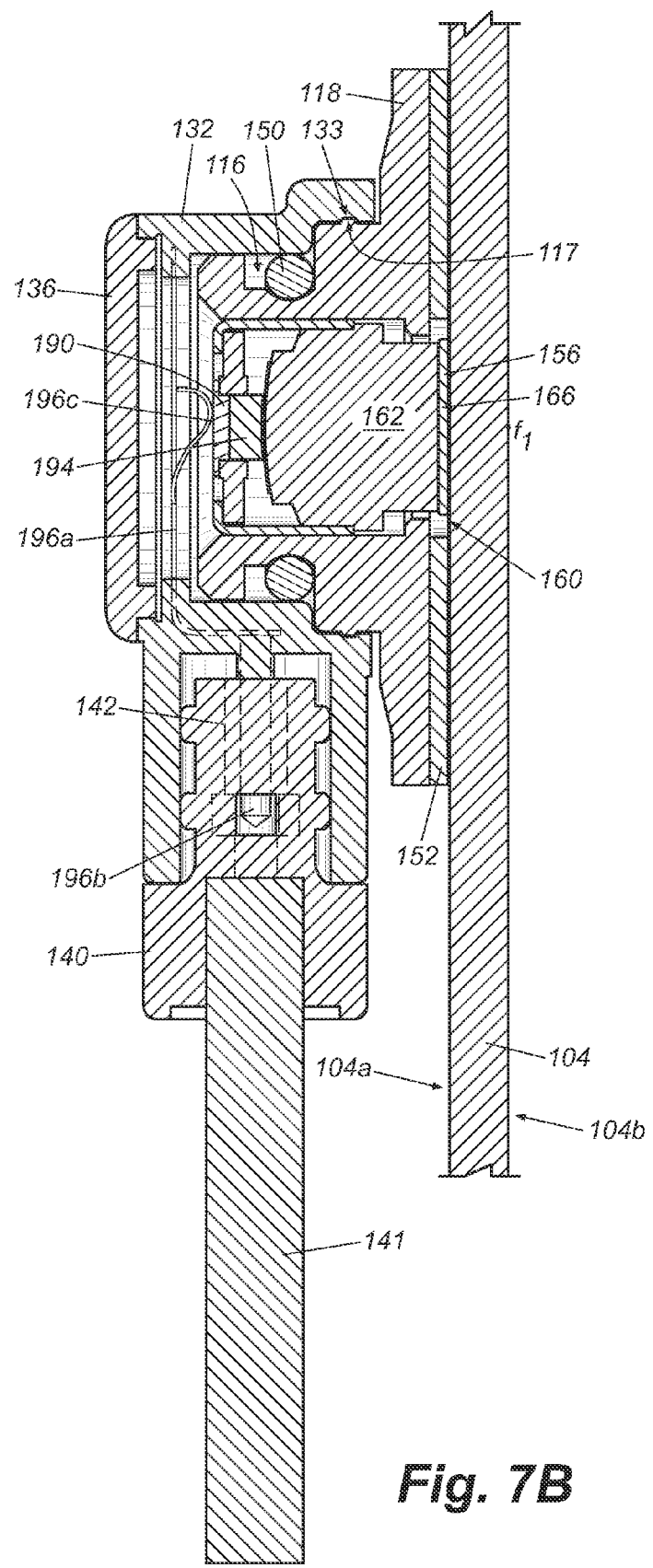
FIG. 7B is a side, cross-sectional view of the fluid level detector as shown in FIG. 7A, positioned adjacent a container wall.

Referring to FIG. 7A, an adhesive layer 152 for securing fluid level detector 100 to a container wall is secured to bottom surface 122 of bottom housing 110. Preferably, adhesive layer 152 comprises a layer of double-sided tape having a pressure-sensitive adhesive on both sides. Double-sided tape layer 152 has the same diameter as bottom surface 122 of base 118 and has an aperture 152 formed at its center. Aperture 152a has a diameter at least equal to that of aperture 120 (FIGS. 7A and 7B). After securing double-sided tape layer 152 to bottom surface 122, a non-stick, peel-away film is adhered to the side of the double-sided tape layer 152 opposite to that which is secured to bottom surface 122. The peel-away film (not shown) is a solid piece of film similar to those typically found on stickers and double-sided tape, that is not removed until fluid level detector 100 is to be installed. As such, the peel-away film inhibits debris, dust, and moisture from entering the housing by way of aperture 120 prior to the use of fluid level detector 100.

A coupling layer 156 is adhered to contact face 166 (FIG. 5A) of lens 162. As shown, the diameter of coupling layer 156 is substantially similar to the diameter of contact face 166 and slightly less than the diameter of aperture 152a formed in the double-sided tape layer 152, as best seen in FIG. 3. Desirable materials for coupling layer 156 are capable of being formed in thin sections to minimize acoustic losses, able to conform to surface irregularities, exhibit low acoustic loss, have acoustic impedances that closely match those of most polymers, and are non-aqueous in nature to facilitate extended periods of use. Examples of suitable coupling materials include: urethane, neoprene, thixotropic glycerin, and high-temperature grease, although it should be appreciated that other suitable materials can be utilized.

Next, transducer 160 is slidably received in central bore 114 of bottom housing 110. Inward motion of transducer 160 is limited by the peel-away surface (not shown), such that coupling layer 156 lies in the same plain as double-sided tape layer 152. Note, the greatest outside diameter of transducer 160 is sized such that transducer 160 readily slides within central bore 114 (FIG. 1).

Referring to FIGS. 1, 7A and 7B, after positioning transducer 160 in central bore 114, top housing 130 is secured to bottom housing 110. Top housing 130 includes a pair of electrical contacts secured therein. For ease of description, only first electrical contact 196 is shown. Preferably, first electrical contact 196 includes a base portion 196a, a male electrode 196b, and a spring 196c. Base portion 196a is securely held by portions of top housing 130. Male electrode 196b extends from base portion 196a and into wiring harness receptacle 134 of top housing 130. Spring 196c extends from base portion 196a and makes contact with tab contact 190 of transducer 160. Spring 196c can be of any suitable configuration, such as a leaf spring or coil spring, that biases the transducer into operative contact with the container. Although spring 196c can be either metallic or non-metallic, preferred embodiments include metal springs such that the spring itself is an electrically conductive element.

The biasing element of the second electrical contact (not shown) depends inwardly from top housing 130 and makes mechanical and electrical contact with conductive sleeve 180 of transducer 160. The second electrical contact also has a male electrode extending outwardly into wiring harness receptacle 134. Engagement of annular groove 133 by annular lip 117 maintains bottom housing 110 and top housing 130 in the assembled position. O-ring 150 is disposed in annular groove 116 between bottom and top housings 110 and 130 and helps maintain the structural integrity of fluid level detector 100.

Figure 8:
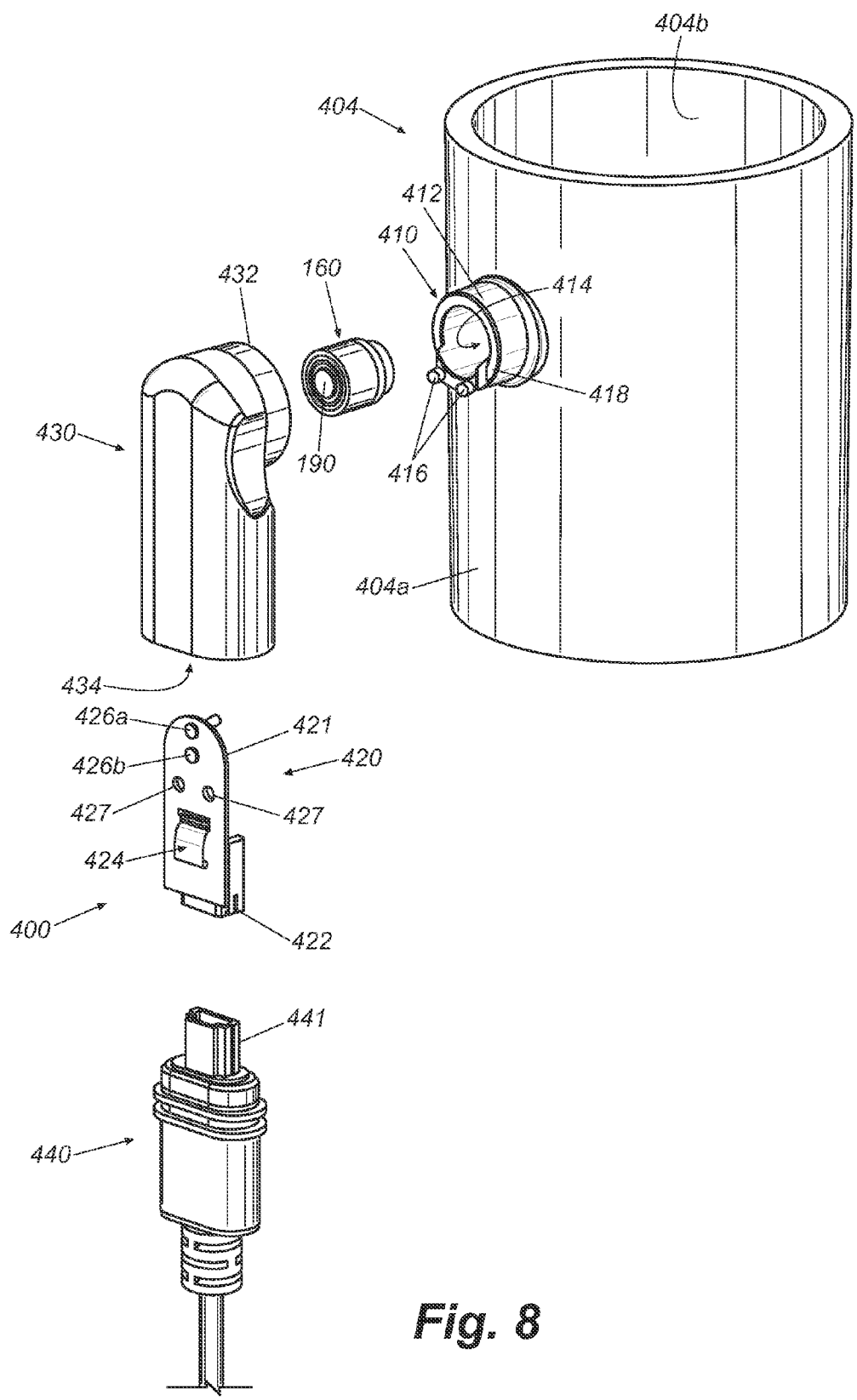
FIG. 8 is an exploded, perspective view of a fluid level detector in accordance with an embodiment of the present invention.
Figure 9:
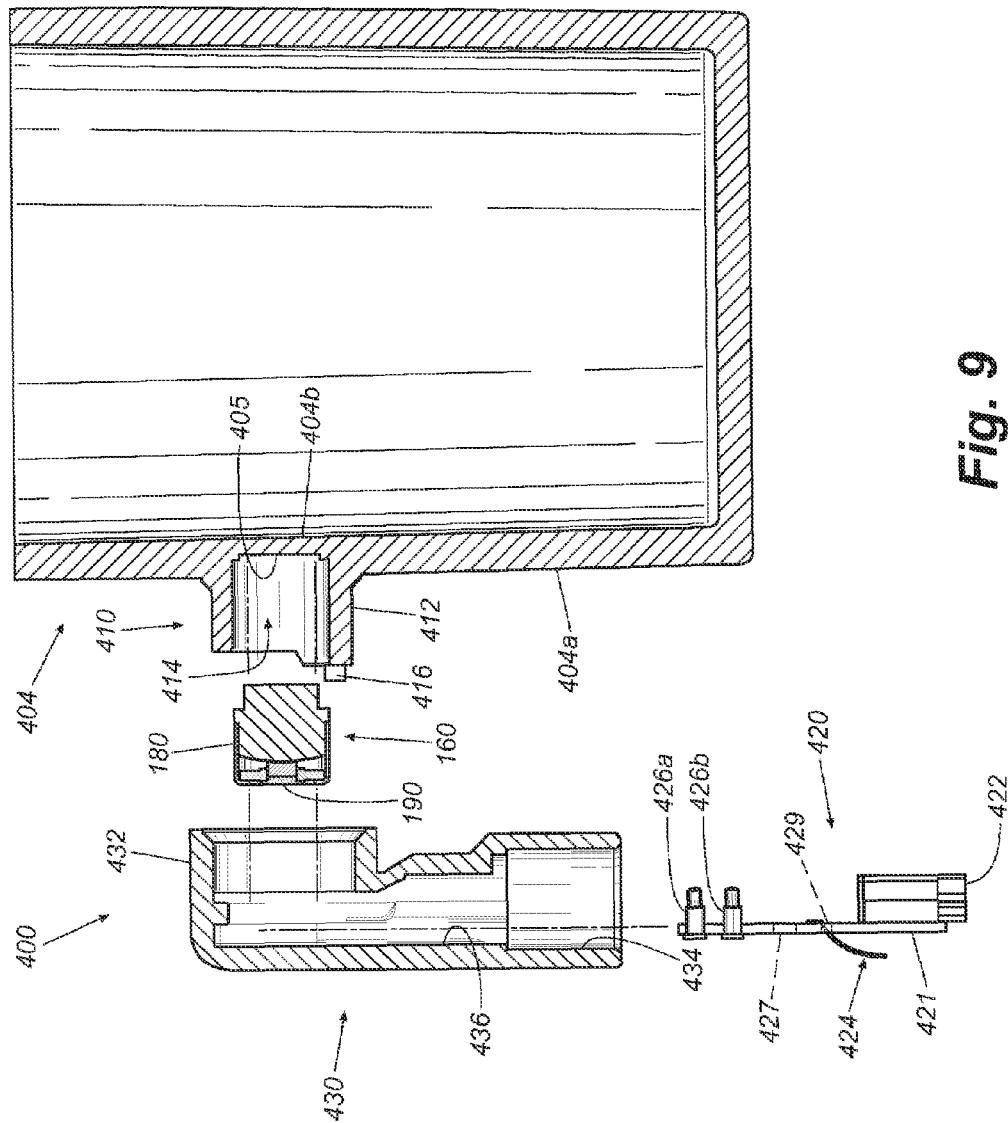
FIG. 9 is an exploded, side cross-sectional view of the fluid level detector as shown in FIG. 8.
Figure 10:
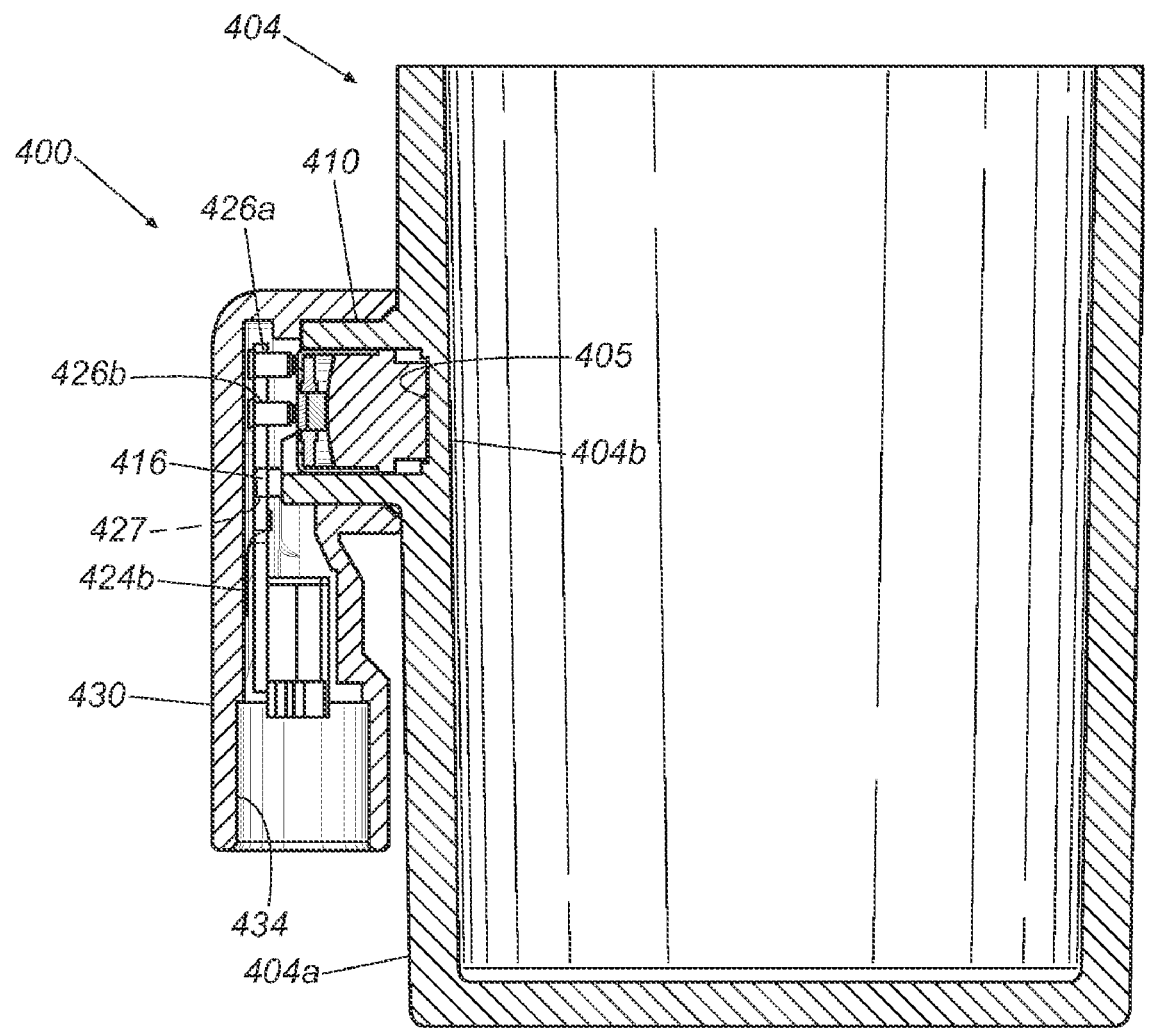
FIG. 10 is a side, cross-sectional view of the fluid level detector as shown in FIG. 8.

Referring now to FIGS. 8 through 10, an alternate embodiment of a fluid level detector 400 includes a bottom housing 410, a contact assembly 420, a top housing 430, a wiring harness 440, and a sensor assembly 160. Sensor assembly 160 comprises an ultrasonic transducer constructed similarly to the one described with regard to fluid level detector 100 (FIG. 1). As such, a description of sensor assembly 160 is not repeated here.

Bottom housing 410 includes a generally cylindrical wall 412 defining a generally cylindrical central bore 414 disposed about the longitudinal center axis of bottom housing 410. Cylindrical wall 412 is integrally formed with container 404 and extends radially outwardly from an outer surface 404a of container 404. Cylindrical wall 412 further defines a cylindrical base surface 405 adjacent container 404. Base surface 405 is both planar and transverse to the longitudinal center axis of bottom housing 410. As best seen in FIG. 9, base surface 405 can be recessed into the wall of container 404 in order to obtain the desired wall thickness at the point of testing, as described in greater detail below. A pair of engagement pins 416 extend axially outward from a top peripheral surface 418 of cylindrical wall 412 such that engagement pins 416 are parallel to the longitudinal center axis of bottom housing 410.

Top housing 430 includes a generally cylindrical wall 432 extending outwardly therefrom. Cylindrical wall 432 is configured to slidably receive cylindrical wall 412 of bottom housing 410. A wiring harness receptacle 434 for slidably receiving wiring harness 440 extends radially outwardly from cylindrical wall 432. A contact assembly cavity 436 also extends outwardly from cylindrical wall 432 and is disposed between cylindrical wall 432 and wiring harness receptacle 434. Contact assembly cavity 436 is configured to slidably receive contact assembly 420 therein in a friction fit. Preferably, top housing 430 is formed from an electrically conductive yet pliant material. For example, a conductive plastic, such as an acrylonitrile butadiene styrene/polycarbonate polymer blend including nickel plated fibers, is used in the present embodiment. The reason for preferably using an electrically conductive material for top housing 430 is discussed in greater detail below. However, it should be appreciated that any suitable non-conductive material, such as various other molded polymers, could be utilized.

As best seen in FIGS. 11A through 11C, contact assembly 420 includes a printed circuit board 421, a universal serial bus (USB) port 422, a grounding terminal 424, and a first and a second spring contact, 426a and 426b, respectively. USB port 422 is secured to a front side 421a of PCB 421 such that it is accessible by way of wiring harness receptacle 434 after contact assembly 420 is inserted into top housing 430. First and second spring contacts 426a and 426b are passed through respective apertures from a back side 421b of PCB 421 and secured thereto by soldering. Each spring contact 426a and 426b includes a spring-biased inner barrel 428a and 428b, respectively, that is axially movable relative to its outer barrel. An alternate embodiment of fluid level detector 400 can include electrical contacts 196 previously discussed with regard to fluid level detector 100 (FIGS. 7A and 7B).

Contact assembly 420 also includes a grounding terminal 424 with a first end 424a secured to front side 421a of PCB 421 by soldering and a second end 424b that passes through a slot 429 formed in PCB 421 such that second end 424b extends outwardly therefrom. As such, second end 424b of grounding terminal 424 contacts an inner surface of top housing 430 when contact assembly 420 is inserted therein (FIG. 10) and a ground trace 444 connects grounding terminal 424 to USB port 422. Because top housing 430 is produced from an electrically conductive material, it is electrically connected to USB port 422 by way of grounding terminal 424 and grounding trace 444. Therefore, top housing 430 shields the operations of fluid level detector 400 from random electrical signals, or "noise," in the operational environment by being grounded through an electrical lead in the USB port 422. First and second electrical traces 442a and 442b electrically connect first and second spring contacts 426a and 426b to USB port 422, respectively. A pair of retention apertures 427 are formed in PCB 421 and are configured to receive retention pins 416 of bottom housing 410 in a friction fit. Interaction of retention pins 416 with retention apertures 427 helps ensure that top housing 430 remains properly secured to bottom housing 410.

As in the previous embodiment, when installing fluid level detector 400 in central bore 414 of bottom housing 410 of the desired container, a coupling layer 156 is first adhered to contact face 166 (FIG. 5A) of lens 162. The diameter of coupling layer 156 is substantially similar to the diameter of contact face 166 and slightly less than the diameter of base surface 405 (FIG. 9). Next, transducer 160 is slidably received in central bore 414 until contact face 166 is adjacent base surface 405. The diameter of base surface 405 is substantially similar to that of contact face 166 such that base surface 405 assists in maintaining transducer 160 in the desired position.

Referring now to FIGS. 9 and 10, after positioning transducer 160 in central bore 414 of bottom housing 410, top housing 430 is secured to bottom housing 410. Note that in FIG. 9 contact assembly 420 is shown separated from top housing 430 for ease of description only. Preferably, after contact assembly 420 is inserted into top housing 430, it is only removable upon application of considerable force. This helps insure that contact assembly 420 remains firmly seated in top housing 430 during repeated insertion and removal of a USB plug 441 (FIG. 8) from USB port 422. Additionally, adhesives may be used to prevent inadvertent removal of contact assembly 420 from top housing 430.

When securing top housing 430 to bottom housing 410, a user first aligns retention apertures 427 with retention pins 416. Top housing 430 is then urged inwardly over bottom housing 410 until retention pins 416 engage retention apertures 427 in a press-fit. With top housing 430 properly positioned, first spring contact 426a makes contact with conductive sleeve 180 and second spring contact 426b makes contact with tab contact 190 of transducer 160. Because inner barrels 428a and 428b are spring biased outwardly, proper electrical contact with transducer 160 is maintained. As well, spring biased inner barrels 428a and 428b urge transducer 160 inwardly into operative contact with base surface 405 on container 404. Alternately, top housing 430 can be secured to bottom housing 410 with adhesives applied between the outer surface of bottom housing 410 and the inner surface of cylindrical wall 432.

Figure 12:
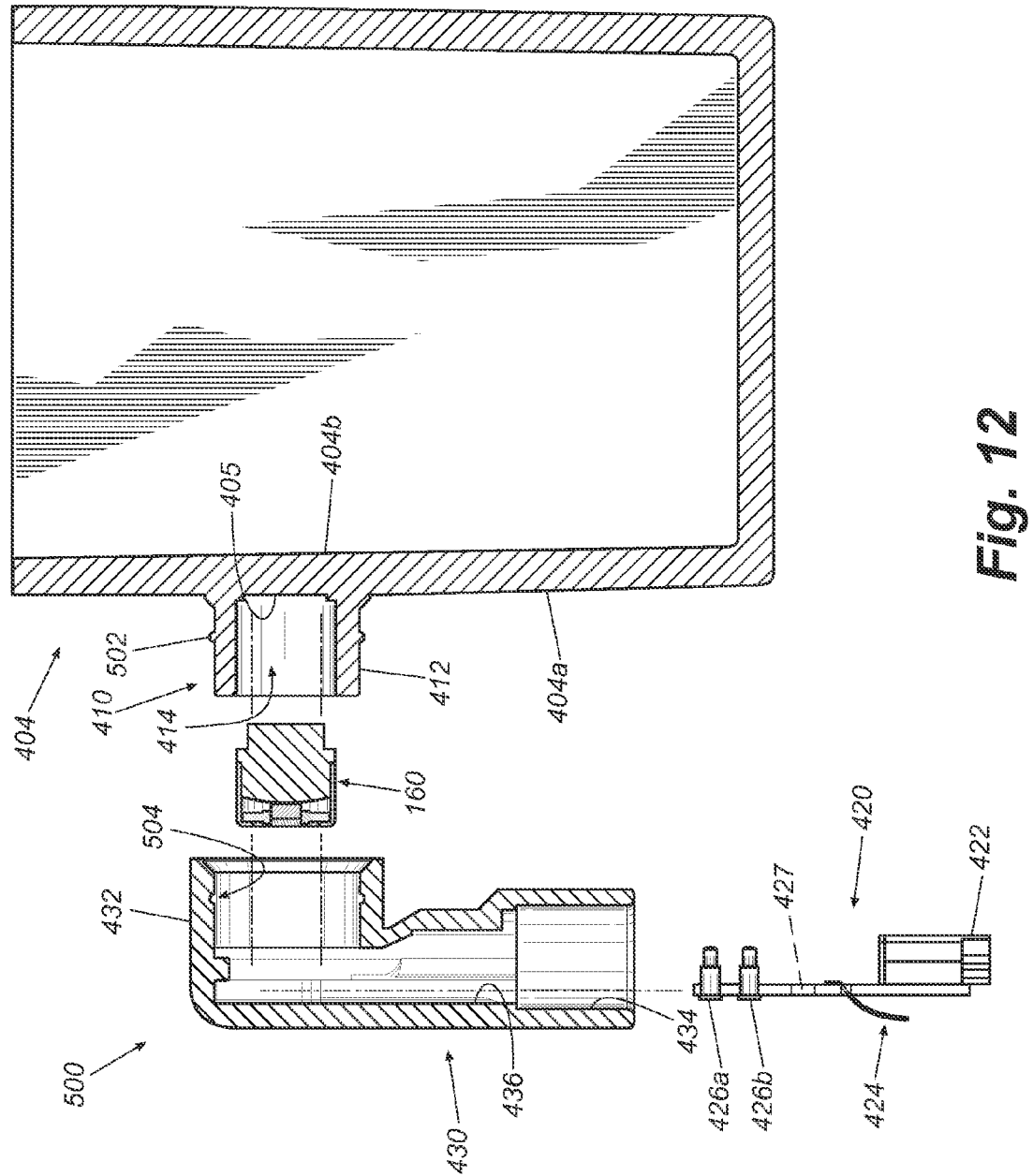
FIG. 12 is a side, cross-sectional view of a fluid level detector in accordance with an embodiment of the present invention.

Referring now to FIG. 12, a fluid level detector 500 is shown for use on a container 404 having a rectangular cross-section. Top housing 430 is secured to a bottom housing 410 by an annular lip 502 on bottom housing 410 that engages an annular groove 504 formed on top housing 430. As shown, base surface 405 of cylindrical central bore 414 of bottom housing 410 lies in the same plane as outer surface 404a of container. However, as in the previously discussed embodiment, fluid level detector 400, base surface 405 of central bore 414 can be recessed into the wall of the container in order to obtain a wall thickness at the point of testing that is thinner than the thickness of the wall surrounding fluid level detector 500.

Operation

The previously discussed embodiments of fluid level detectors operate in substantially the same manner. As such, each embodiment need not be addressed directly and only fluid level detector 100 shown in FIGS. 7A and 7B will be referred to while discussing the operation of the detectors. Any notable differences are addressed as necessary.

Prior to use, and referring to FIGS. 7A and 7B, fluid level detector 100 is first applied to a wall 104 of the container containing the liquid to be monitored. Preferred embodiments of the present fluid level detector 100 are used to monitor fluid levels in polymer containers or containers constructed of other similar materials having maximum wall thicknesses of approximately 0.150 inches ("). For such containers, preferred embodiments of fluid detector 100 include piezoelectric film elements 170 measuring approximately 0.230" long, 0.125" wide, and 0.004" thick, and constructed of PVDF. However, these dimensions can be varied for container walls of varying thicknesses.

As is known in the art, materials attenuate acoustic energy as the energy passes there through. Moreover, acoustic energy at higher frequencies is attenuated over shorter distances within a given material than is acoustic energy at lower frequencies. As noted above, preferred embodiments of fluid level detector 100 include a piezoelectric film element 170 composed of a PVDF, which has a relatively high natural operating frequency of approximately 10,000,000 Hz (10 MHz). Thus, preferred embodiments of fluid detector 100 are typically used on polymer containers having maximum wall thicknesses of up to 0.150" so that adequate return signals exist for fluid detection, as discussed hereafter.

Increasing the size (length by width) of piezoelectric film element 170 permits fluid level detector 100 to be used with greater wall thicknesses since a greater amount of wall material is required to attenuate the larger amount of acoustic energy that is generated. This requires a corresponding increase in the domed top surface of lens 162 to accommodate the larger piezoelectric film and focus its resulting acoustic signals. The amount of acoustic energy generated by the transducer can also be increased while maintaining the size of both the domed top surface of lens 162 and piezoelectric film element 170 by "stacking" multiple film elements. By stacking multiple piezoelectric film elements atop each other and electrically connecting them, either in parallel or in series, the amount of acoustic energy generated will be the cumulative amount of that energy generated by each piezoelectric film.

Fluid level detector 100 can also be used with greater wall thicknesses when piezoelectric film element 170 is composed of piezoelectric materials with lower natural frequencies since the generated acoustic energy travels farther through the same materials than does the high frequency acoustic energy before being detrimentally attenuated. Moreover, for a given wall thickness, acoustic energy at lower frequencies provides larger return signals than does acoustic energy at higher frequencies.

Prior to installing fluid level detector 100 on the container wall, the point on container wall 104 corresponding to the desired level of detection is determined. The installer then removes the peel-away surface (not shown) disposed on the bottom face of double-sided tape layer 152. With the peel-away surface removed, force exerted on transducer 160 by springs 196c (only one is shown) urges transducer 160 along central bore 114 such that contact face 166 of lens 162 extends beyond double-sided tape layer 152, as shown in FIG. 7A. Outward motion of transducer 160 caused by springs 196c ceases when annular ledge 168 abuts the inwardly depending ledge of bottom housing 110 that defines aperture 120. Note, contact face 166 and coupling layer 156 extend slightly beyond double-sided tape layer 152 such that full contact between transducer 160 and the container wall 104 is possible.

Fluid level detector 100 is then pressed firmly against container wall 104 at the desired location. Double-sided tape layer 152 secures fluid level detector 100 to container wall 104, as shown in FIG. 7B. As fluid level detector 100 is pressed against container wall 104, contact between container wall 104 and contact face 166, by way of coupling layer 156, urges transducer 160 back inside central bore 114. Springs 196c maintain pressure on transducer 160, thereby ensuring proper positioning of contact face 166 adjacent the outer surface 104a of container wall 104. As such, springs 196c serve to bias piezoelectric film element 170 operatively toward outer surface 104a of wall 104. For fluid detectors 400 and 500 shown in FIGS. 10 and 12, respectively, first and second spring contacts 426a and 426b maintain pressure on transducer 160 to ensure proper positioning of contact face 166 adjacent base surface 405.

By biasing piezoelectric film element 170 operatively toward wall 104, springs 196c bias the piezoelectric film element 170 either directly against wall 104 or against intermediate components, such as lens 162 and coupling layer 156 in the embodiment shown. These components in turn couple the acoustic signal generated by piezoelectric film element 170 to wall 104. Although in the latter case springs 196c still bias piezoelectric film element 170 in the direction of wall 104, it is possible that in other arrangements springs 196c will bias piezoelectric film element 170 in a direction other than toward wall 104, yet still into coupling elements such that the acoustic signal generated by piezoelectric film element 170 is nevertheless coupled to the wall. In such arrangements, springs 196c are said to bias piezoelectric film element 170 operatively toward the wall although they do not bias piezoelectric film element 170 directionally toward the wall.

Wiring harness 140 includes female electrode receptacles 142 (only one is shown). Wiring harness 140 is slidably received inside wiring harness receptacle 134 of top housing 130 such that female electrode receptacles 142 are connected with male electrodes 196b. Electronic signals to and from fluid level detector 100 may now be transmitted to the detector as desired. For fluid level detectors 400 (FIG. 10) and 500 (FIG. 12), wiring harness 440 includes a USB plug 441 that is slidably received in USB port 422 in order to transmit electronic signals to and from the detectors.

In preferred embodiments, the input electrical signal to fluid level detector 100 is a ten volt peak-to-peak (ground to +10 volts) pulse lasting approximately 50 nanoseconds, or a twenty-four volt (+12 v to −12 v) square wave lasting approximately 100 nanoseconds, (hereafter, "excitation signal"). As shown in FIGS. 7A and 7B, the excitation signal is applied across opposing top and bottom sides 172 and 174 of piezoelectric film 170 by way of two independent electrical paths. In the illustrated embodiment, the first electrical path is as follows: from first electrical contact 196 to tab contact 190 by way of spring 196c; from tab contact 190 to conductive pad 194; and from conductive pad 194 to first electrode layer 176 formed on top surface 172 of piezoelectric film element 170 (as shown in FIG. 6). The second path is as follows: from the second electrical contact (not shown) to conductive sleeve 180 by way of the spring, from conductive sleeve 180 to conductive layer 163 disposed on domed surface 164; and from domed surface 164 to second electrode layer 178 formed on bottom surface 174 of piezoelectric film element 170 (as shown in FIG. 6).

Application of the excitation signal creates vibrations in piezoelectric film element 170. PVDF is used for piezoelectric film element 170 because of its inherently low acoustic impedance and natural frequency of approximately 10 MHz. Typical acoustic impedance values for PVDF range from $2.5 \times 10^6$ to $3.0 \times 10^6$ Rayleighs (2.5 to 3.0 Mrayls), making the piezoelectric film desirable for transmitting acoustic signals into walls of similar-impedance polymer containers with minimal losses. Most polymers have impedance valves of between about 1.5 and 3.0 Mrayls.

Because piezoelectric film element 170 is secured to domed surface 164, vibrations of piezoelectric film element 170 create pressure fluctuations in the material of lens 162. As previously noted, lens 162 is preferably constructed of a polystyrene or other like material such that the acoustic impedance of lens 162 will be substantially similar to that of piezoelectric film element 170 and that of wall 104 of the container. Substantially similar acoustic impedance values for the various materials facilitate the passage of acoustic energy as each transmitted signal propagates into the adjacent materials. Preferably, acoustic impedance values of the materials used to construct piezoelectric film element 170, lens 162, and container wall 104 are within 2.5 Mrayls of each other. Thus, each acoustic signal generated by the excitation of piezoelectric film element 170 propagates from one component to the next with acceptable energy loss, insuring effective operation of fluid detector 100.

The generated pressure fluctuations propagate through lens 162 until they reach contact face 166. As shown in FIGS. 5A and 5B, in a preferred embodiment, each point along domed surface 164 is equidistant from a focal point ($f_1$) located on contact face 166 of lens 162, this distance being the radius of curvature of the domed surface 164. Lens 162 thereby focuses a maximum amount of pressure fluctuation at focal point ($f_1$) as the acoustic signal travels from domed surface 164 toward contact face 166. It should be noted that focal point ($f_1$) need not be located on contact face 166 of lens 162. For example, preferred embodiments have focal points ($f_1$) located on inner surface 104b of container wall 104, as shown in FIG. 7B, provided the width of both coupling layer 156 and container wall 104 are known. Similarly, focal points ($f_1$) may be selected that are located within lens 162, wall 104, or the fluid to be detected.

The piezoelectric element of the preferred embodiments is a piezoelectric film element 170. As is known in the art, acoustic output power of piezoelectric films is generally less than that of piezoelectric ceramics in response to comparable input signals. By focusing the pressure fluctuations transferred from piezoelectric film element 170 to lens 162 at focal point ($f_1$), however, lens 162 transfers the relatively lower pressure across the surface of the piezoelectric film element to a higher pressure at focal point ($f_1$). Lens 162 thereby delivers a sufficiently strong acoustic signal to container wall 104 to facilitate operation of fluid detector 100.

Lens 162 also functions as an acoustic standoff. More specifically, lens 162 is dimensioned such that reflected acoustic signals are not received at piezoelectric film element 170 until after piezoelectric film element 170 has ceased vibrating in response to application of the excitation pulse. Lens 162 facilitates operation of fluid level detector 100 by insuring that reflected signals for determining the presence or absence of fluids are not received until after the transmission phase of piezoelectric film element 170 has subsided.

In the preferred embodiment, the radius of curvature of domed surface 164 of lens 162 is measured from focal point ($f_1$) on inner surface 104b of wall 104 (FIG. 7B) and is approximately 0.40". The preferred radius of curvature takes into account the height of lens 162 (0.250" in the preferred embodiment), the thickness of coupling layer 156, and the thickness of wall 104. Considerations for the height of lens 162 can include adequate distance to accomplish acoustic standoff for the frequency of the acoustic signal being used and potentially the overall dimensions of fluid level detector 100. For example, greater lens heights can be required to provide sufficient acoustic standoff for lower frequency acoustic signals used with containers having greater wall thicknesses to avoid detrimental attenuation.

Although, ideally, no acoustic impedance mismatch would exist at the respective interfaces between the materials of interfaces piezoelectric film element 170, lens 162, and container wall 104, there will normally be at least slight impedance mismatches. Transmission of the acoustic signal will therefore be affected as it passes from one material to the next. For example, an impedance mismatch likely exists at the boundary of contact face 166 and outer surface 104a of container wall 104, where lens 162 and wall 104 are operatively coupled to allow transmission of acoustic signals therebetween. The impedance mismatch between the materials of lens 162 and container wall 104 causes a portion of the energy of the acoustic signal to be reflected back through lens 162, eventually reaching piezoelectric film element 170. The first reflection of acoustic energy causes vibration of piezoelectric film element 170. In response, piezoelectric film element 170 creates an electrical signal across its electrodes that is sent to an electronics module, as discussed hereafter, as a single pulse or echo. That portion of the acoustic signal that is not reflected at contact face 166 of lens 162 continues to propagate into the next material layer.

Transmission of acoustic signals from one material to the next is facilitated when acoustic impedances of the materials are matched and when the two abutting surfaces are in full contact. Coupling layer 156 is therefore preferably disposed between contact face 166 and outer surface 104a of container wall 104 and is preferably composed of a material that is sufficiently pliant to accommodate surface irregularities between contact surface 166 and outer surface 104b, thereby preventing the formation of air pockets between the abutting surfaces that would otherwise degrade propagation of acoustic signals.

The material of coupling layer 156 is also chosen to minimize the effects of any acoustic impedance mismatch between the materials of lens 162 and container wall 104. It is expected that fluid level detector 100 will be used to detect fluid levels in containers constructed of various polymers having acoustic impedance valves in the range of 1.5 to 3 Mrayl. In the event the acoustic impedance of the container wall is not sufficiently matched to the acoustic impedance of lens 162, a coupling material can be used to improve the impedance match. For example, the acoustic impedance of coupling layer 156 is preferably between the acoustic impedance values of lens 162 and the container wall such that the acoustic signal encounters the overall mismatch incrementally rather than all at once. This facilitates transfer of acoustic energy from lens 162 to coupling layer 156 and from coupling layer 156 to the container wall.

The coupling layer, although chosen to enhance acoustic impedance matching, results in two interfaces at which a slight mismatch nevertheless occurs—between lens 162 and coupling layer 156 and between coupling layer 156 and the container wall. The two interfaces result in two reflected signals when the acoustic signal from the piezoelectric element passes through the coupling layer to the wall. As indicated above, the reflected acoustic energy travels back through lens 162 and eventually causes vibration of piezoelectric film element 170. Preferably, however, coupling layer 156 is sufficiently thin that the second reflection, i.e. due to the coupling layer 156\container wall 104 interface, arrives at the piezoelectric film at substantially the same time as does the first reflected signal, i.e. due to the lens 162/coupling layer 156 interface, and for purposes of this discussion, the two reflections are considered to be a single reflection. As described in more detail below, the electronics module is configured to disregard this combined reflection.

The remainder of the acoustic signal that has not been reflected at the above noted material interfaces propagates into and through container wall 104 until reaching inner surface 104b, at which point a third reflection of acoustic energy occurs. The amplitude of the reflected acoustic energy is largely dependent upon the size of the acoustic impedance mismatch that occurs between the material of wall 104 and the material disposed in the container opposite fluid level detector 100.

Air has an approximate acoustic impedance of 407 rayls. Most polymers have acoustic impedances of between 1.5 to 3.0 Mrayls. Thus, a large acoustic impedance mismatch occurs at the inner surface 104b of wall 104 when air is located within the container opposite fluid level detector 100. Thus, the overwhelming majority of energy of the acoustic signal will be reflected at inner surface 104b when the container's liquid level falls below the position at which detector 100 is attached to the wall. Water, on the other hand, has an approximate acoustic impedance of 1.48 Mrayls, notably closer to the values of acoustic impedances for most polymers, and the reflected energy from an interface between inner surface 104b and water is therefore small as compared to the reflected energy when air is present. Most fluids have acoustic impedance values similar to that of water, meaning they have essentially the same effect on the acoustic signal as does water. Therefore, when water or other fluid is present opposite fluid level detector 100, the overwhelming majority of acoustic energy is transmitted from container wall 104 into that fluid, where it eventually dissipates.

The third reflected signal (i.e. due to the interface of the inner wall surface and air or liquid) propagates back through container wall 104, coupling layer 156, and lens 162 until it reaches piezoelectric film element 170. As before, the third reflected signal causes vibration of piezoelectric film element 170, resulting in an electrical signal being created across the film's electrodes and sent to the electronic module. The voltage of the signal created by piezoelectric film element 170 is proportional to the amount of energy reflected at inner surface 104b of wall 104. Accordingly, a large voltage signal received at the electronic module indicates that air or other gas is present in the container at the level of fluid level detector 100. Conversely, a small voltage signal received at the electronic module indicates that a fluid is present in the container opposite fluid level detector 100.

Figure 13A:
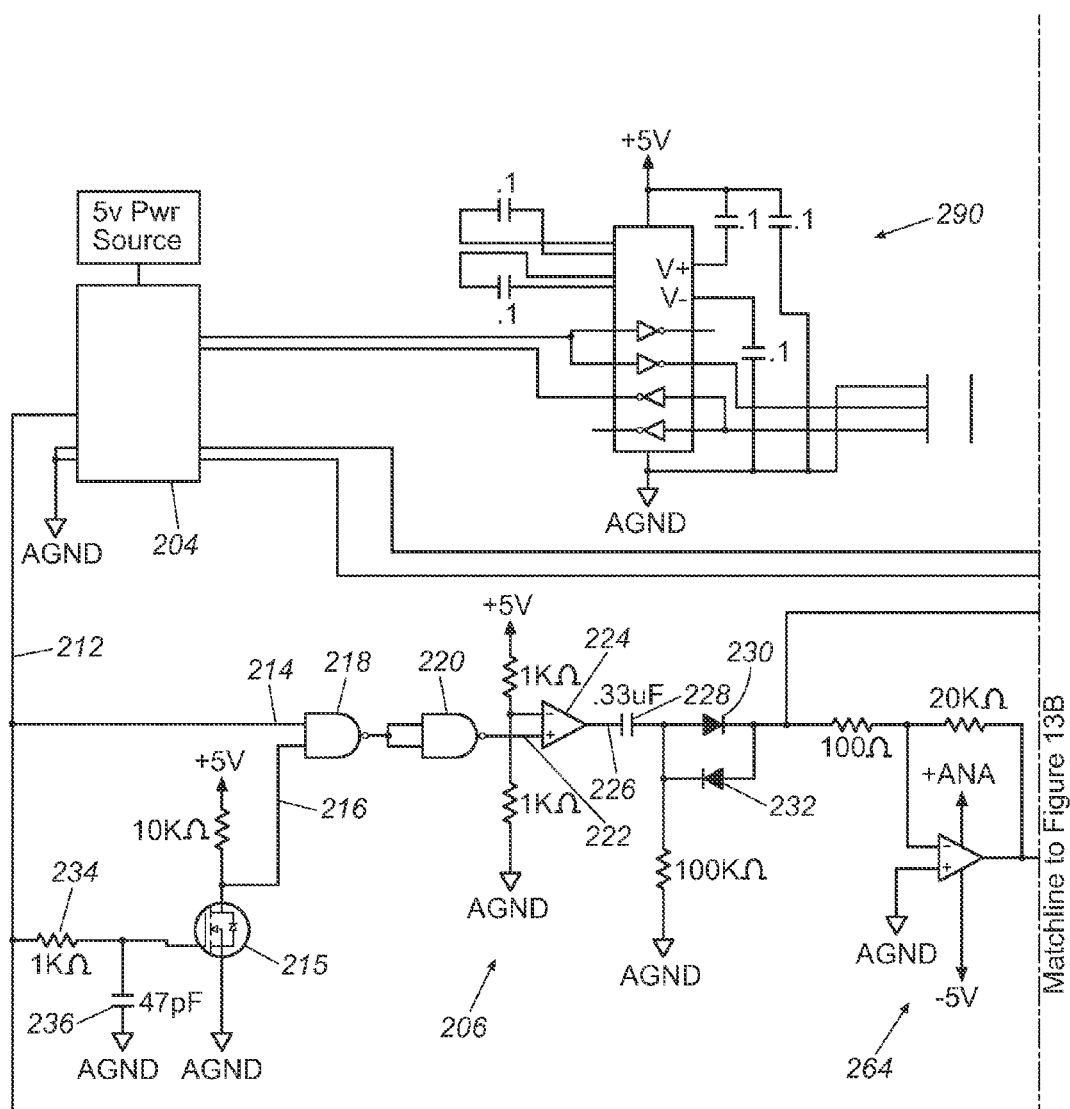
FIGS. 13A and 13B are an electrical schematic of an electronic module for use with a fluid level detector as shown in FIG. 1.
Figure 13B:
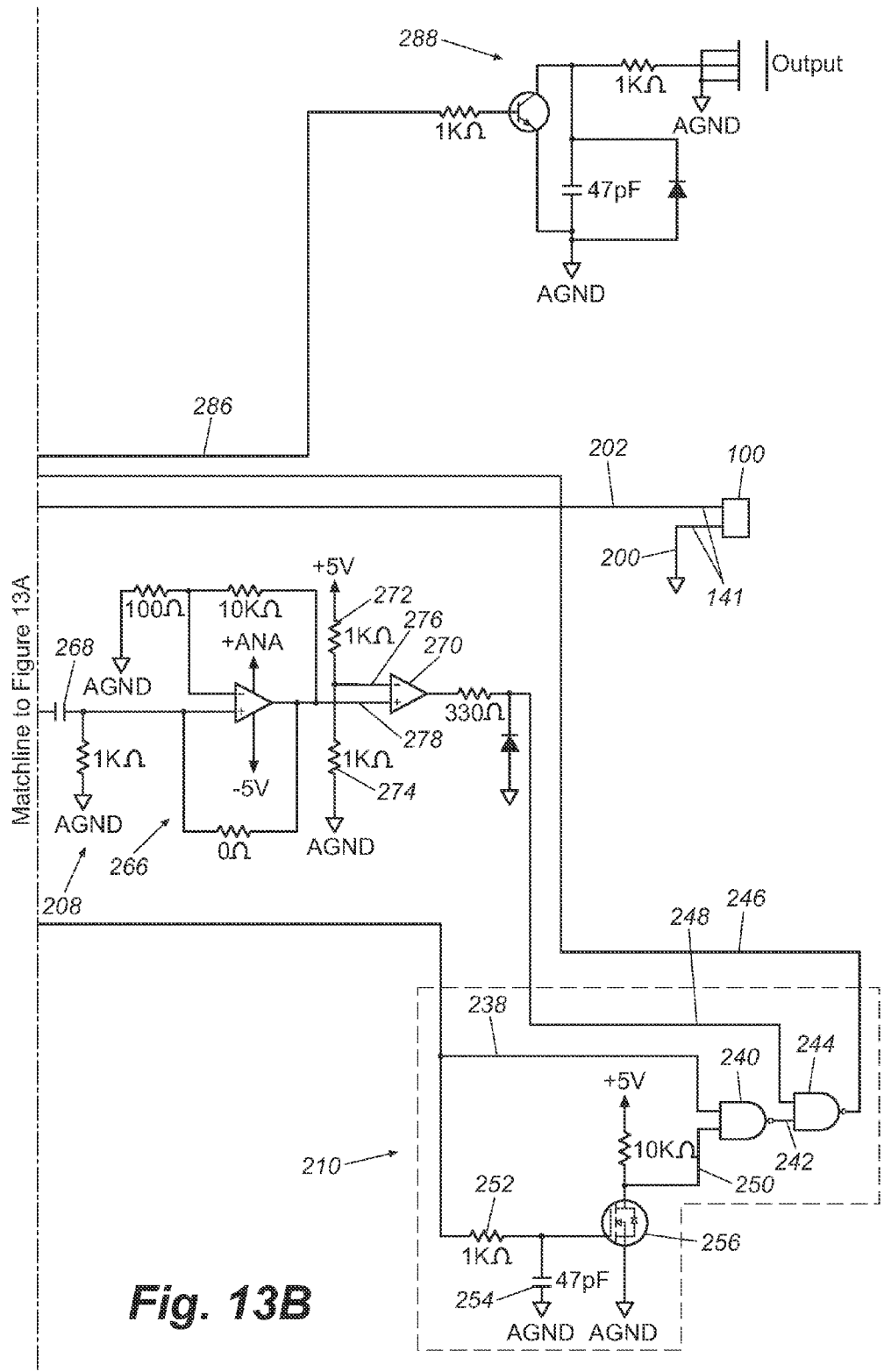

Operation of the electronics module will now be discussed with respect to FIGS. 13 through 15. Referring initially to FIG. 13, a dual wire bundle 141 output from wiring harness 140 (FIG. 1) includes a ground wire 200 and a signal wire 202 that carries both the input electrical signal to the transducer and the output electrical signal corresponding to the reflected ultrasonic signal. Wire 202 electrically connects through the wiring harness to the spring 196c (FIG. 7A, or spring contact 426b for level detectors 400 and 500 in FIGS. 10 and 12, respectively) that contacts tab contact 190, whereas wire 200 electrically connects through the wiring harness to conductive sleeve 180 (FIG. 7A) by the second spring (not shown, or spring contact 426a for level detectors 400 and 500). Dual wire bundle 141 extends from fluid level detector 100 to a printed circuit board remote from the detector and upon which the circuitry shown in FIG. 13 is disposed. The circuitry shown in FIG. 13 is also on a printed circuit board that is remote from fluid level detectors 400 (FIG. 10) and 500 (FIG. 12).

A processor 204 (in a preferred embodiment, a four megahertz single chip microcontroller) disposed on the printed circuit board controls an excitation circuit 206, a detection circuit 208 and a blanking period generator circuit 210 through the output of high or low signals (for example, +5 volts or ground) on a trace 212. Generally, this system alternates between an excitation mode, in which excitation circuit 206 provides an input electrical signal to detector 100, and a detection mode, in which detection circuit 208 receives and notifies the microprocessor of signals corresponding to acoustic echoes from a gas interface at the inner container wall opposite the detector. In a preferred embodiment, the microprocessor triggers the excitation mode once per second such that the electronics module checks the output of fluid level detector 100 for liquid level approximately once per second, although the timing can vary as desired.

Immediately prior to the excitation mode, the output of microprocessor 204 on trace 212 is low such that input 214 to a NAND gate 218 is low. The low signal at 212 maintains an input 216 high through a switch such as a MOSFET 215. The low signal at 214 results in a low signal on line 202 such that no excitation signal is provided to the piezoelectric film of fluid level detector 100. At the beginning of the excitation mode, however, the microprocessor's output to trace 212 goes high, thereby immediately bringing input 214 high. Since input 216 is normally high, this causes the output of NAND gate 218 to go low. An inverter 220 changes the low signal to high at an input 222 to a comparator 224 that level-shifts the signal to +10 volts at 226. A capacitor 228 AC-couples the excitation signal, which passes through a diode 230 to input line 202 and, then, to the electrodes driving the piezoelectric film.

Diodes 230 and 232 isolate the return signal from the excitation circuit. As described in more detail below, the return signal on line 202 generated by vibrations of the piezoelectric film in fluid level detector 100 are of relatively low power such that the return signal is insufficient to activate diode 232.

The duration of the high portion of the input electrical signal on line 202 is defined by the RC time constant of a resistor 234 and a capacitor 236. More specifically, the high signal on trace 212 does not immediately cause MOSFET 215 to bring input 216 low. Instead, 216 goes low when capacitor 236 charges sufficiently to activate MOSFET 215. When input 216 goes low, the output of NAND gate 218 goes high, causing the outputs of inverter 220 and comparator 224 to go low. In the illustrated embodiment, the RC time constant of register 234 and capacitor 236 is approximately 50 nanoseconds. Thus, the duration of the input electrical signal pulse output by excitation circuit 206 is approximately 50 nanoseconds.

Blanking period generator circuit 210 defines the duration of the excitation mode. Immediately prior to the excitation mode, when the signal on trace 212 is low, an input 238 to a NAND gate 240 is low. Thus, an input 242 to a NAND gate 244 is high, and the value of an output 246 from NAND gate 244 therefore depends upon the signal at an input 248. Input 248 is the output of detection circuit 208 and, as described in more detail below, is in either a high or low state, depending upon whether detection circuit 208 has received a sufficiently strong signal on line 202. When detection circuit 208 detects such a signal, the detection circuit places a high signal on trace 248. This causes NAND gate 244 to transition from high to low at 246, thereby notifying microprocessor 204 that a signal has been received indicating that fluid level detector 100 has detected air or other gas on the opposite side of the container wall from the detector.

Accordingly, as long as trace 242 remains high, NAND gate 244 passes the detection signal from detection circuit 208 to the microprocessor. This condition exists during the detection mode, which is therefore defined by the time period during which either the signal on trace 212 is low or an input at 250 is low.

Again referring to the time immediately prior to the excitation mode, the signal on trace 212 is low. Output 242 of NAND gate 240 is therefore high, and NAND gate 244 therefore gates the output of detection circuit 208 to microprocessor 204. When microprocessor 204 drives the signal on trace 212 high, however, input 238 to NAND gate 240 immediately goes high. Input 250 to NAND gate 240 is normally high during detection mode, and so NAND gate 240 drives trace 242 to a low signal. This causes output 246 of NAND gate 244 to be high regardless of the signal from detection circuit 208 on trace 248. Accordingly, changes on line 202 caused by return signals detected by fluid level detector 100 have no effect on output 246, and microprocessor 204 therefore does not receive signals on 246 indicating that such return signals have occurred. In other words, the transition to the high signal on trace 212 starts a period during which blanking period generator 210 blocks detection circuit 208 from reporting detection of a return acoustic signal by fluid level detector 100. This condition is the excitation mode.

The duration of the excitation mode is defined by the RC time constant of a resistor 252 and a capacitor 254. A MOSFET 256 normally maintains the signal on trace 250 high when the signal on 212 is low. When 212 goes high, the RC network 252/254 prevents the new high signal from immediately driving the signal on trace 250 low. When capacitor 254 eventually charges sufficiently to cause MOSFET 256 to drive the signal on trace 250 low, the low signal causes NAND gate 240 to drive the signal on trace 242 high regardless of the high signal on 238. Thus, NAND gate 244 again passes the output of detection circuit 208 to microprocessor 204, and the system has returned to detection mode. Microprocessor 204 thereafter drives the signal on trace 212 low, thereby resetting excitation circuit 206 prior to triggering the next excitation mode on the one second interval.

In a preferred embodiment, the RC time constant of resistor 252 and capacitor 254 defines the duration of the excitation mode to $5.0 \times 10^{-6}$ seconds (5 ms). This period may vary as desired, however, for example depending upon characteristics of fluid level detector 100 and the timing of signals it is likely to detect. For example, and referring also to FIG. 15A, the excitation period (indicated at 258), and therefore the RC time constant of resistor 252 and capacitor 254, should be sufficiently long so that blanking period generator circuit 210 blocks the responses of detector circuit 208 to both the input electrical signal generated by excitation circuit 206 and to signals returned on line 202 as a result of ringing of the piezoelectric film following the excitation signal.

As described above, the input electrical signal from excitation circuit 206 is a 10 volt pulse lasting approximately 50 nanoseconds. Detection circuit 206 detects this relatively large signal as it is being output onto line 202. Furthermore, the piezoelectric film in fluid level detector 100 vibrates for some period of time after the end of the 50 nanosecond pulse. This ringing of the film creates a signal across the film's electrodes that is returned to the detection circuit over line 202. Thus, during excitation mode, detection circuit 206 sees a relatively large signal, indicated at 260 in FIG. 15A, that would otherwise cause the detection circuit to incorrectly send a signal to microprocessor 204 indicating an acoustic echo had been received. Because blanking period generator 210 maintains a low signal on trace 242 during the excitation mode, however, NAND gate 244 does not gate this signal to the microprocessor, which therefore sees no false echo report during this period, as indicated at 262 in FIG. 15B. To assure that detection circuit 208 does not report a false echo, the RC time constant defined by resistor 252 and capacitor 254 should be established so that blanking period generator 210 blocks signals detected by detection circuit 208 for a period longer than the time during which signals resulting directly from the input electrical signal (i.e. not from an acoustic echo following the input electrical signal) are expected to be sufficiently high that detector circuit 208 would otherwise incorrectly provide a signal to microprocessor 204 indicating an acoustic echo had been received.

Detection circuit 208 is comprised of a pair of amplifier stages 264 and 266, an AC coupling capacitor 268, and a comparator 270. Because signals generated by the piezoelectric film in fluid level detector 100 are of relatively low power, for example on the order of 1 to 2 millivolts, amplifier stages 264 and 266 apply an approximately four hundred times gain to the signal received from fluid level detector 100 over line 202. Comparator 270 then compares the amplified signal to a predetermined voltage level defined by divider resistors 272 and 274 at 276. The voltage level at 276 is preferably set so that signals generated by acoustic echoes from the transducer and the outer wall of the container are ignored, while the stronger signals resulting from the container's inner wall surface and air trigger a change in the detector circuit's output.

As described above, the acoustic echo from the interface between the lens and coupling material, and between the coupling material and the container wall outer surface, is weaker than an acoustic echo resulting from an air interface with the container inner wall surface. The first echo therefore results in weaker vibrations in the piezoelectric film than does the second echo, and the first echo therefore generates a lower voltage signal on line 202. Accordingly, the first echo results in an amplified signal at the input 278 to comparator 270, indicated at 280 in FIG. 15B, having a lower voltage level than an amplified signal, indicated at 282, that results from an acoustic echo from the air interface. The voltage level, indicated at 284, defined by the divider is set higher than the expected level of the first amplified signal (and also higher than the expected level of an amplified signal resulting from an echo from a liquid interface at the container's inner wall surface) but less than the expected level of the second amplified signal. Accordingly, comparator 270 remains low upon receipt of a signal resulting from an acoustic echo from the container wall's outer surface (or from a liquid interface at the container wall's inner surface) but outputs a high signal on trace 248 upon receipt of a signal corresponding to an acoustic echo from the interface between the container wall's inner surface and air. Because the electronic module is now in detection mode, the signal on trace 242 to NAND gate 244 is high. Thus, the transition of the signal on trace 248 from low to high upon receipt of an acoustic echo from an air interface drives the output signal from NAND gate 244 on trace 246 from high to low. During the detection mode, this transition notifies microprocessor 204 that detector 100 has detected a condition at which fluid level inside the container has fallen below the level of the detector. Microprocessor 204 then outputs a signal indicating this condition on a line 286 to an output circuit 288 that drives a notification device such as a lamp, audible device or other peripheral device. Alternatively, or additionally, microprocessor 204 can communicate with a remote processor through an RS-232 circuit 290.

In one preferred embodiment, microprocessor 204 repeatedly checks the signal on trace 246 and does not change the state of its output until detecting a change on trace 246 at five consecutive reads. This inhibits false responses due to jitter in the digital circuitry.

Figure 14A:
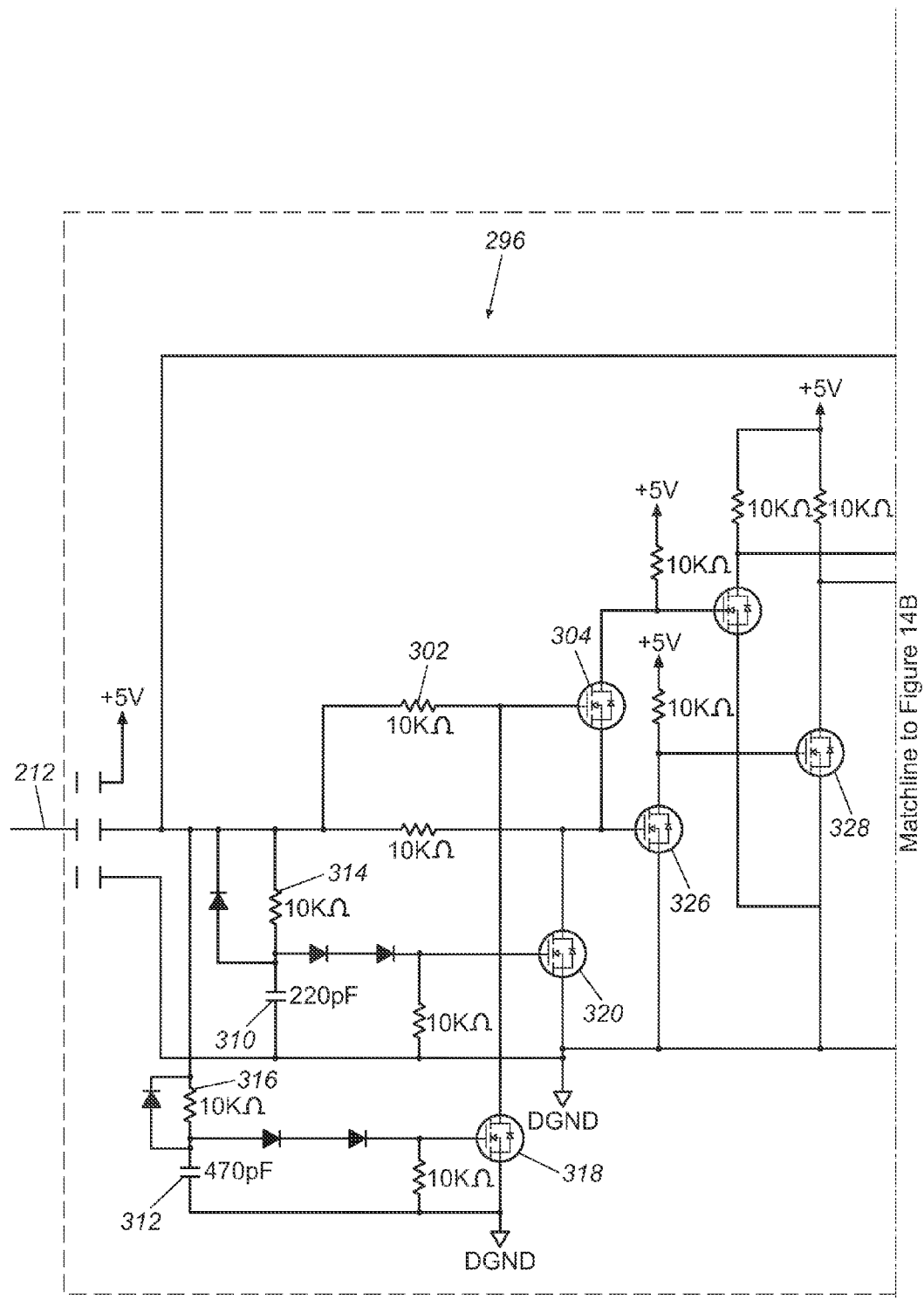
FIGS. 14A and 14B are an electrical schematic of an excitation circuit for use in an electronic module as shown in FIGS. 13A and 13B.
Figure 14B:
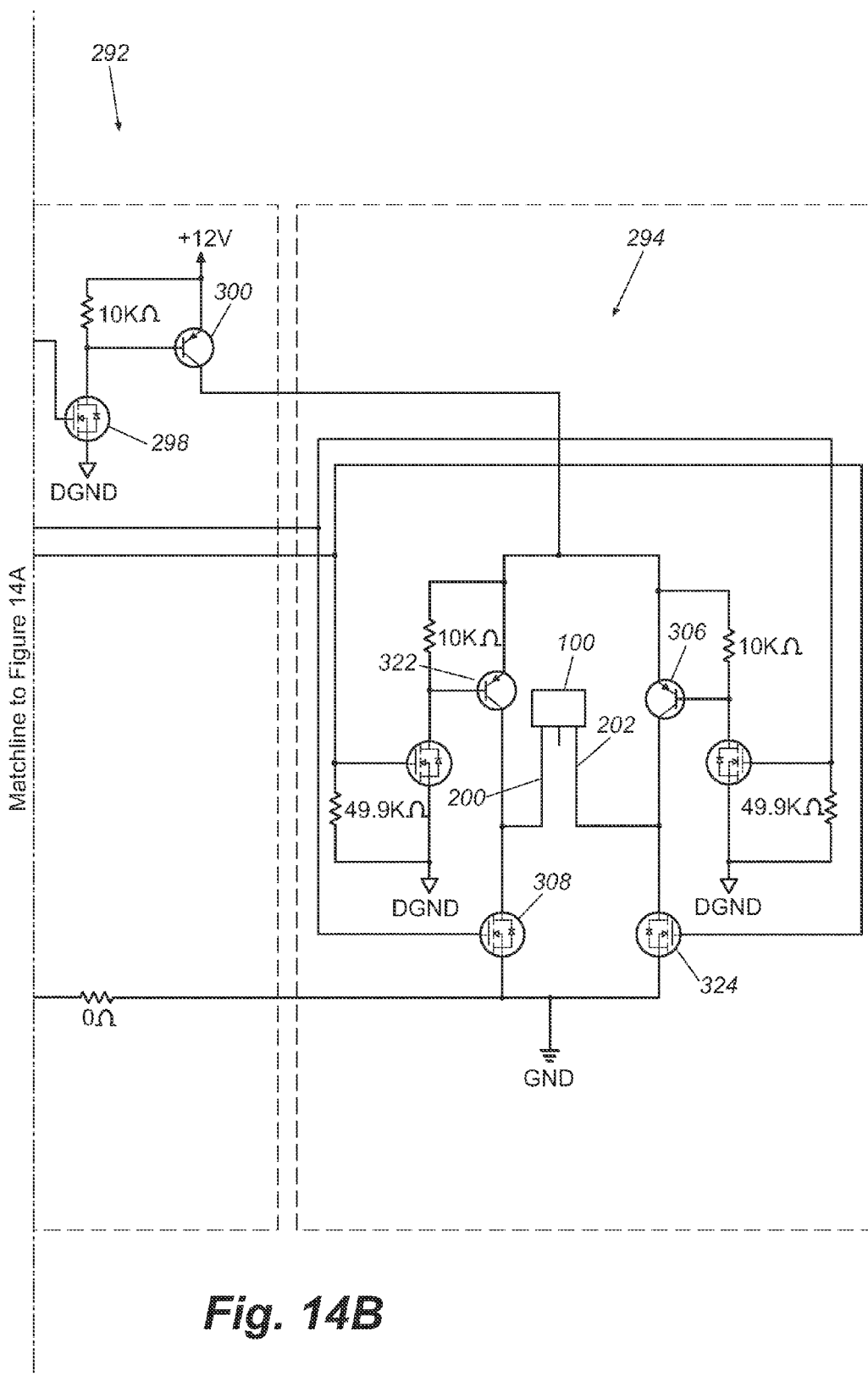
Figure 15A:
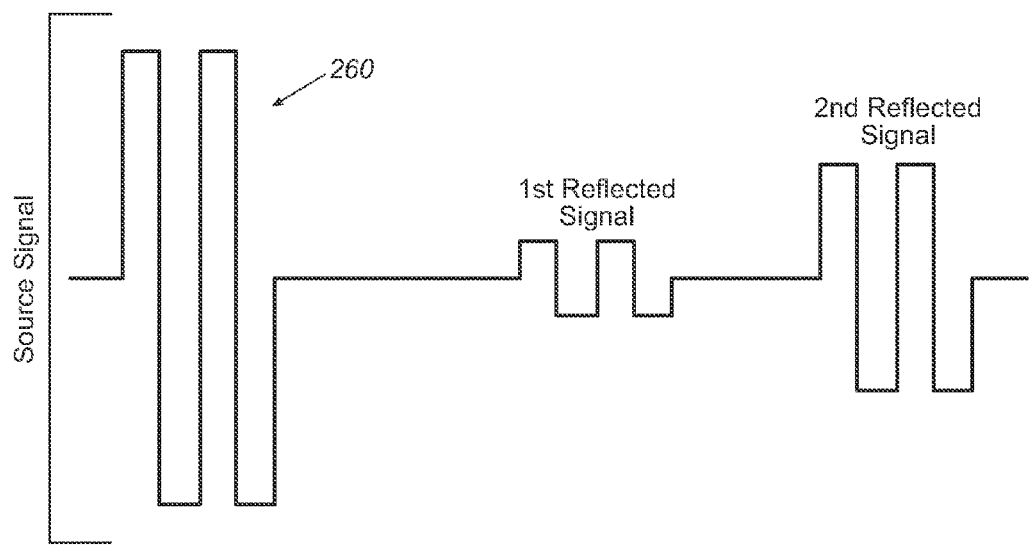
FIGS. 15A and 15B are graphical representations of signals processed by the electronic module as shown in FIGS. 13A and 13B and 14A and 14B.
Figure 15B:
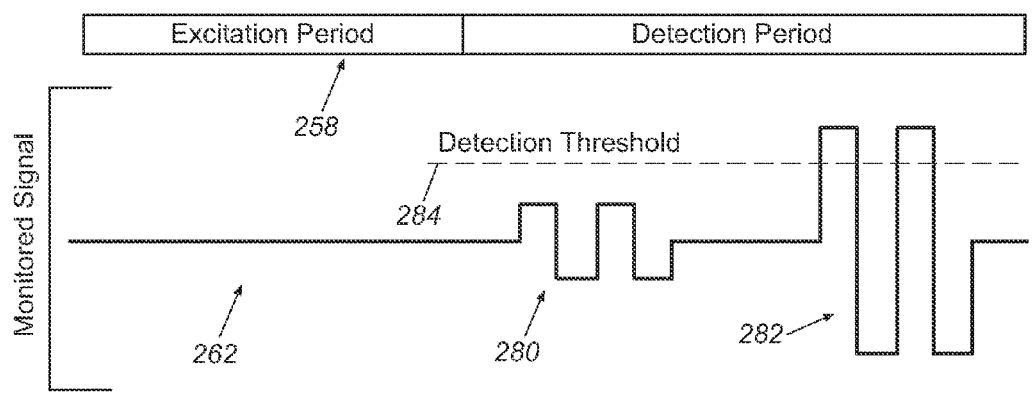

In a still further preferred embodiment, and referring to FIGS. 13 and 14, excitation circuit 206 is replaced by an excitation circuit 292 to provide a square wave electrical signal rather than a pulse. Excitation circuit 292 is comprised of an H-bridge circuit 294 controlled by a timing circuit 296. H-bridge circuit 294 applies a square wave to fluid level detector 100 across lines 200 and 202 that varies between −12 volts and +12 volts.

Prior to the excitation mode, the signal on trace 212 is low. This causes timing circuit 296 to de-activate the H-bridge circuit such that no input electrical signal is provided to the detector. When microprocessor 204 applies a high signal to trace 212 at the beginning of the excitation mode, however, the high signal immediately turns on switches 298 and 300 (which may be, for example, high speed MOSFET's or bipolar transistors), thereby applying a 12 volt signal from the power source to the H-bridge. An approximate two nanosecond delay caused by a resistor 302 and switch 304 allows the H-bridge circuit to power up through switches 298 and 300 before the occurrence of subsequent transitions.

The activation of switch 304 turns on switches 306 and 308 (again which, for example, may be MOSFET's or bipolar transistors) in the H-bridge, thereby applying a +12 volt signal to the piezoelectric film across lines 200 and 202. Meanwhile, capacitors 310 and 312 charge through resistors 314 and 316, respectively. Capacitor 312 charges first, thereby turning on switch 318. This grounds the gate of switch 304 and thereby turns off switches 306 and 308.

The time constant defined by resistor 314 and capacitor 310 (approximately 50 nanoseconds) is such that, at this point, a switch 320 turns on, thereby turning on switches 322 and 324 through switches 326 and 328. This applies a −12 volt portion of the square wave across lines 200 and 202. Microprocessor 204 then (approximately 50 nanoseconds later) drives the signal on trace 212 low, thereby deactivating the H-bridge circuit.

In the configuration of the blanking period generator circuit shown in FIG. 13, the low signal on trace 212 also returns the electronic module to receive mode. In the event that ringing in the piezoelectric film following the end of the square wave does not result in a return signal of sufficient magnitude to require blocking of the detection circuit by the blanking period generator, or if the microprocessor is programmed to ignore such a response, this is acceptable. In the event, however, that it is desired to block the detection for a certain period of time in order to block signals resulting from ringing in the piezoelectric film following the input electrical signal, blanking period generator circuit 210 is preferably modified so that the output of NAND gate 244 remains high for a sufficiently long period after the end of the input electrical signal.

While one or more preferred embodiments of the fluid level detector have been described above, it should be understood that any and all equivalent realizations of the fluid level detector are included within the scope and spirit thereof. For example, the piezoelectric film and lens can be replaced by one or more piezoelectric ceramic elements. Because ceramic elements produce stronger electrical signals, amplification in the electronics module can be reduced or eliminated. Thus, the depicted embodiments are presented by way of example only and are not intended as limitations on the fluid level detector. It should be understood that aspects of the various one or more embodiments may be interchanged either in whole or in part. Therefore, it is contemplated that any and all such embodiments are included in the present disclosure as may fall within the literal or equivalent scope of the appended claims.

What is claimed:

1. A fluid detector for determining a presence of a fluid within a container having a wall with an outer surface and an inner surface, the fluid detector comprising:
    a piezoelectric element that outputs a first ultrasonic signal in response to an input electrical signal;
    a lens with an upper portion and a lower portion;
    a generally cylindrical wall being integral with and extending outwardly from the outer surface of the wall of the container, the generally cylindrical wall defining a housing with a cylindrical central bore having a base surface adjacent the outer surface of the wall of the container; and
    wherein the piezoelectric element is coupled to the upper portion of the lens so that, when the lens is disposed within the cylindrical central bore adjacent the base surface such that the lens is intermediate the piezoelectric element and the wall, the lens focuses the first ultrasonic signal toward the wall so that the first ultrasonic signal enters the wall; and
    wherein the piezoelectric element is disposed in a predetermined position adjacent the outer surface of the wall such that the piezoelectric element receives a second ultrasonic signal from the wall that results from the first ultrasonic signal and that is affected in a predetermined manner by presence or absence of fluid at the inner surface of the wall, wherein the piezoelectric element generates an output electrical signal corresponding to the second ultrasonic signal.

2. The fluid detector as in claim 1, wherein the piezoelectric element comprises a piezoelectric film.

3. The fluid detector as in claim 2, wherein the piezoelectric element and the lens are disposed within the cylindrical central bore of the housing.

4. The fluid detector as in claim 3, wherein the base surface of the cylindrical central bore is coplanar with the outer surface of the wall of the container.

5. The fluid detector as in claim 3, wherein the piezoelectric film comprises a polyvinylidene fluoride copolymer.

6. The fluid detector as in claim 3, wherein the piezoelectric film, the lens and the wall of the container have substantially similar acoustic impedances.

7. The fluid detector as in claim 3, wherein the lens focuses the first ultrasonic signal on the inner surface of the wall.

8. The fluid detector as in claim 3, wherein the cylindrical central bore extends into the wall of the container such that the base surface of the cylindrical central bore is disposed between the outer surface and the inner surface of the wall of the container.

9. The fluid detector as in claim 8, wherein the outer surface of the wall of the container from which the generally cylindrical wall extends is curved.

10. The fluid detector as in claim 9, wherein the base surface of the generally cylindrical bore is planar.

11. The fluid detector as in claim 3, further comprising a top housing including a generally cylindrical inner wall that is configured to slidably receive the housing defined by the generally cylindrical wall of the container.

12. The fluid detector as in claim 11, further comprising:
a retention pin extending axially from an outer peripheral surface of the housing defined by the generally cylindrical wall of the container; and
a retention aperture defined by the top housing;
wherein the retention aperture is configured to receive the retention pin in a friction fit such that the top housing is secured on the housing defined by the generally cylindrical wall of the container.

13. A fluid detector for determining a presence of a fluid, the fluid detector comprising:
a container with a wall with an outer surface and an inner surface, a portion of the wall extending outwardly from the outer surface of the wall and defining a housing with a cylindrical central bore with a base surface disposed proximal to the wall of the container;
a piezoelectric element that outputs a first ultrasonic signal in response to an input electrical signal; and
a lens with an upper portion and a lower portion;
wherein the piezoelectric element is coupled to the upper portion of the lens so that, when the lens is disposed within the cylindrical central bore of the housing such that the lens is intermediate the piezoelectric element and the wall, the lens focuses the first ultrasonic signal toward the wall so that the first ultrasonic signal enters the wall.

14. The fluid detector as in claim 13, wherein the piezoelectric element comprises a piezoelectric film.

15. The fluid detector as in claim 14, wherein the piezoelectric film comprises a polyvinylidene fluoride copolymer.

16. The fluid detector as in claim 13, further comprising an ultrasonic detector that, when disposed in a predetermined position adjacent the outer surface of the wall, receives a second ultrasonic signal from the wall that results from the first ultrasonic signal and that is affected in a predetermined manner by presence or absence of fluid at the inner surface of the wall, wherein the ultrasonic detector generates an output electrical signal corresponding to the second ultrasonic signal.

17. The fluid detector as in claim 16, wherein the base surface of the cylindrical central bore of the housing is recessed into the wall of the container.

18. The fluid detector as in claim 16, wherein the base surface of the cylindrical central bore of the housing is coplanar with the outer surface of the wall of the container.

19. The fluid detector as in claim 16, wherein the ultrasonic detector is comprised of the piezoelectric element and the lens and the predetermined position is within the cylindrical central bore of the housing.

20. The fluid detector as in claim 16, further comprising a top housing including a generally cylindrical inner wall that is configured to slidably receive the housing that defines the cylindrical central bore.

* * * * *